(12) United States Patent
Anderson, Jr. et al.

(10) Patent No.: US 10,029,967 B2
(45) Date of Patent: *Jul. 24, 2018

(54) TRI-SUBSTITUTED AROMATIC-CONTAINING MONOMERS, COPOLYMERS AND METHODS FOR USE

(71) Applicant: RHODIA OPERATIONS, Paris (FR)

(72) Inventors: Eugene J. Anderson, Jr., Marlton, NJ (US); Derek Pakenham, Hamilton, NJ (US); Nemesio Martinez-Castro, Bristol, PA (US); Jose P. Ruiz, Burlington, NJ (US); Michael Rhodes, Chalfont, PA (US)

(73) Assignee: Rhodia Operations, Paris (FR)

( * ) Notice: Subject to any disclaimer, the term of this patent is extended or adjusted under 35 U.S.C. 154(b) by 82 days.

This patent is subject to a terminal disclaimer.

(21) Appl. No.: 14/661,808

(22) Filed: Mar. 18, 2015

(65) Prior Publication Data

US 2015/0266804 A1 Sep. 24, 2015

Related U.S. Application Data

(60) Provisional application No. 61/954,857, filed on Mar. 18, 2014, provisional application No. 61/954,852, filed on Mar. 18, 2014.

(51) Int. Cl.

| | |
|---|---|
| C08F 20/30 | (2006.01) |
| C08F 22/12 | (2006.01) |
| C07C 43/205 | (2006.01) |
| C08K 3/04 | (2006.01) |
| C08K 5/13 | (2006.01) |
| C07C 69/54 | (2006.01) |
| C07C 37/14 | (2006.01) |
| C07C 41/03 | (2006.01) |
| C08F 220/30 | (2006.01) |

(52) U.S. Cl.
CPC .......... *C07C 43/2055* (2013.01); *C07C 37/14* (2013.01); *C07C 41/03* (2013.01); *C07C 69/54* (2013.01); *C08F 20/30* (2013.01); *C08F 22/12* (2013.01); *C08K 3/04* (2013.01); *C08K 5/13* (2013.01); *C08F 2220/306* (2013.01)

(58) Field of Classification Search
CPC ..... C07C 43/2055; C07C 37/14; C07C 41/03; C07C 69/54; C08F 20/30; C08F 22/12; C08K 3/04; C08K 5/13

USPC .......... 560/221; 524/560, 556; 526/320, 318
See application file for complete search history.

(56) References Cited

U.S. PATENT DOCUMENTS

| | | | |
|---|---|---|---|
| 3,937,283 | A | 2/1976 | Blauer et al. |
| 4,579,670 | A | 4/1986 | Payne |
| 5,551,516 | A | 9/1996 | Norman et al. |
| 5,770,760 | A | 6/1998 | Robinson |
| 2009/0186968 | A1* | 7/2009 | Zong ........................ C07C 43/23 524/131 |
| 2014/0336335 | A1* | 11/2014 | Stanion ................. C08F 220/04 525/330.2 |

FOREIGN PATENT DOCUMENTS

| | | |
|---|---|---|
| EP | 0186255 A2 | 2/1985 |
| EP | 0177111 A2 | 4/1985 |
| EP | 0149173 A1 | 7/1985 |
| JP | 60229969 A2 | 11/1985 |
| JP | 61241370 A2 | 10/1986 |
| JP | 2004505127 A | 2/2004 |
| RU | 2246504 C1 | 2/2005 |
| WO | 0035863 A1 | 6/2000 |
| WO | 2013072696 A1 | 5/2013 |

OTHER PUBLICATIONS

G. Poehlen, "Emulsion Polymerization", Encyclopedia of Polymer Science and Engineering, vol. 6, pp. 1-51 (John Wiley & Sons, Inc., NY, NY, 1986).
A. S. Sarac, "Redox Polymerization", Progress in Polymer Science 24 (1999), pp. 1149-1204.
Edited by Raymond E. Kirk and Donald F. Othmer, Encyclopedia of Chemical Technology, Third Edition, John Wiley & Sons, vol. 16, pp. 248-273 (entitled "Nuts"), Copyright 1981.
"Oilfield Applications", Encyclopedia of Polymer Science and Engineering, vol. 10, pp. 328-366 (John Wiley & Sons, Inc., New York, NY., 1987).

* cited by examiner

*Primary Examiner* — Kelechi Egwim

(57) ABSTRACT

Disclosed are novel tri-substituted aromatic-alkoxylated monomers, polymers made with the novel tri-substituted aromatic-alkoxylated monomers, pH responsive polymers made with the novel tri-substituted aromatic-alkoxylated monomers, and related methods. Also disclosed is an aqueous coating composition including at least one latex polymer derived from at least one monomer copolymerized or blended with alkali swellable acrylate copolymer. Also provided is a method of preparing an aqueous coating composition such as a latex paint including the above components.

19 Claims, No Drawings

TRI-SUBSTITUTED AROMATIC-CONTAINING MONOMERS, COPOLYMERS AND METHODS FOR USE

CROSS-REFERENCE TO RELATED APPLICATIONS

This application claims the benefit of U.S. Provisional Patent Application No. 61/954,857 filed Mar. 18, 2014, incorporated herein by reference in its entirety, and claims the benefit of U.S. Provisional Patent Application No. 61/954,852 filed Mar. 18, 2014, incorporated herein by reference in its entirety.

FIELD OF THE INVENTION

The present invention relates to novel monomers, copolymers comprising such monomers, as well as compositions and methods using such copolymers in various applications.

BACKGROUND OF THE INVENTION

Rheological additives are chemical compositions, which, added even in small amounts, modify a liquid system's rheological properties, such as viscosity and response to shear. Such additives or thickeners may be used in a variety of liquid systems including aqueous systems such as paints, aqueous inks, and personal care products and compositions for treating subterranean formations. The additives improve the rheological properties by also affecting the dispersion, suspension and emulsification of pigments, binders and other solids within a vehicle.

Hydrophobically modified alkali swellable emulsion (HASE, also known as Hydrophobically modified alkali soluble) polymer systems and alkali soluble emulsion (ASE) polymer systems are commonly employed to modify the rheological properties of aqueous emulsion systems. These polymers are substantially insoluble in water at a low pH. However, at higher pH they become swellable or soluble in water and thus exhibit thickening behavior. Under the influence of a base, organic or inorganic, the HASE particles gradually swell and expand to form a three-dimensional network by intermolecular hydrophobic aggregation between HASE copolymer chains and/or with components of the emulsion. This network, combined with the hydrodynamic exclusion volume created by the expanded HASE chains, produces a thickening effect. This network is sensitive to applied stress so it breaks down under shear and recovers when the stress is relieved. Such rheological properties are particularly desirable for paints and coatings because they make the formulation easy to apply onto a surface while providing the thickness needed for uniform coverage and avoid spattering.

These alkali-swellable and alkali-soluble polymers are carboxyl functional polymers synthesized by free radical polymerization. Generally, HASE copolymer systems can be prepared from the following monomers: (a) an ethylenically unsaturated carboxylic acid, (b) a nonionic ethylenically unsaturated monomer, and (c) an ethylenically unsaturated hydrophobic monomer.

Latex is an example of an emulsion polymer which is a water-based polymer dispersion. Latex paints are used for a variety of applications including interior and exterior, and flat, semi-gloss and gloss applications. Latex is a stable dispersion (colloidal emulsion) of rubber or plastic polymer microparticles in an aqueous medium. Latexes may be natural or synthetic.

SUMMARY OF THE INVENTION

In one aspect, described herein are unsaturated monomers according to structure (D.I):

$$R^{18}\text{-}R^{14}\text{-}R^{13}\text{-}R^{12}\text{-}R^{11} \quad \text{(D.I)}.$$

$R^{12}$ is absent or is a bivalent linking group, $R^{13}$ is bivalent polyether group, $R^{14}$ is absent or is a bivalent linking group;

$R^{18}$ is a moiety having a site of ethylenic unsaturation; and $R^{11}$ is according to structure D.XII

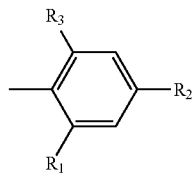

D.XII wherein $R_1$, $R_2$ and $R_3$ are independently selected from H, any of following structures D.XIIa, D.XIIb, D.XIIc, D.XIId:

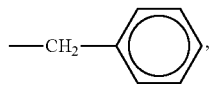

D.XIIIa

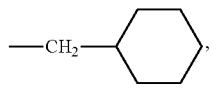

D.XIIIb

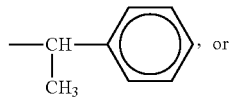

D.XIIIc

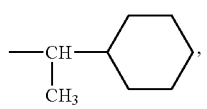

D.XIIId or a $C_2$-$C_{30}$ branched or linear alkyl group or alkenyl group;

wherein at least one of $R_1$, $R_2$ and $R_3$ is the $C_2$-$C_{30}$ branched or linear alkyl group or alkenyl group, and at least one of $R_1$, $R_2$ and $R_3$ is selected from structure D.XIIa, D.XIIb, D.XIIc, or D.XIId.

In another aspect, described herein are unsaturated monomers according to structure (D.I):

$$R^{18}\text{—}R^{14}\text{-}R^{13}\text{-}R^{12}\text{-}R^{11} \quad \text{(D.I)}.$$

$R^{12}$ is absent or is a bivalent linking group, $R^{13}$ is bivalent polyether group, $R^{14}$ is absent or is a bivalent linking group;

$R^{18}$ is a moiety having a site of ethylenic unsaturation; and $R^{11}$ a tri-substituted aromatic group according to the structure D.XII

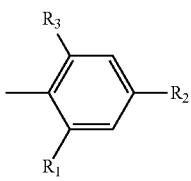

wherein $R_1$, $R_2$ and $R_3$ are independently selected from the following structures D.XIIa, D.XIIb, D.XIIc, D.XIId:

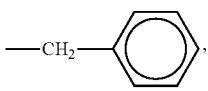

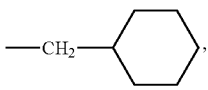

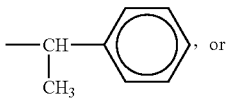

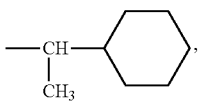

or a $C_2$-$C_{30}$ branched or linear alkyl group or alkenyl group; wherein at least one of $R_1$, $R_2$ and $R_3$ is the $C_2$-$C_{30}$ branched or linear alkyl group or alkenyl group, and at least one of $R_1$, $R_2$ and $R_3$ is selected from structure D.XIIa, D.XIIb, D.XIIc, or D.XIId.

In one embodiment, $R_{12}$ is —$(CH_2)_xO$—, wherein x is an integer from 1 to 20 (e.g., use of styrenated benzyl alcohols)

In another embodiment, $R_{12}$ is —$CH_2CH(OH)CH_2O$— or —$CH_2CH(CH_2OH)O$— (e.g., use of epichlorohydrin as coupling agent)

In one embodiment, $R_{13}$ is:

—$[CH(R_{20})CH(R_{21})O]_x$— wherein x is an integer of from 0 to 100, and $R_{20}$ and $R_{21}$ are independently selected from any of the following:

H; —$CH_2OH$; phenyl; —$CH_2Cl$;

a $C_1$-$C_{30}$ straight or branched alkyl or alkenyl;

—$CH_2OR_{22}$ wherein $R_{22}$ is $C_1$-$C_{30}$ straight or branched alkyl or alkenyl, phenyl, or alkyl substituted phenyl; or R'COOCH$_2$— where R' is $C_1$-$C_{30}$ straight or branched alkyl or alkenyl.

In another aspect, the invention is directed to pH responsive copolymer of a mixture of unsaturated copolymerizable monomers, the unsaturated copolymerizable monomers comprising, based on total weight of monomers:

A. about 0 to 60 weight percent, preferably 5 to 30 weight percent or 10 to 45 weight percent, of at least one $C_3$-$C_8$ alpha beta-ethylenically unsaturated acidic monomer, preferably a $C_3$-$C_8$ alpha beta-ethylenically unsaturated carboxylic acid monomer;

B. about 15 to 70 weight percent, typically 20 to 50 weight percent, of at least one non-ionic, copolymerizable $C_2$-$C_{12}$ alpha, beta-ethylenically unsaturated monomer; and C. about 0.01 to 50 weight percent (wt %), or in another embodiment 0.05 to 30 weight percent, or in another embodiment 0.5 to 10 weight percent, or in another embodiment 1 to 10 weight percent, or in another embodiment 0.5 to 9 weight percent, or in another embodiment 0.5 to 7 weight percent, or in another embodiment 4 to 10 weight percent, of at least one non-ionic ethylenically unsaturated hydrophobic monomer as described herein.

The pH responsive copolymer is also known as a HASE copolymer.

The present invention also includes compositions such as aqueous dispersions comprising this pH responsive copolymer. In particular the invention is also directed using the pH responsive copolymer as an additive for latex binders, paints and aqueous coatings. This pH responsive copolymer additive is used a thickener during formulation of the latex binders, paints and aqueous coatings, compositions for treating subterranean formations, home care and personal care. The pH responsive copolymer, in one embodiment, improves thickening efficiency in aqueous coating formulations, meaning less of the pH responsive copolymer is needed as compared with other thickeners to achieve the same rheological profile (or thickening properties). The effect of this thickening efficiency, in one embodiment, results in improved water sensitivity properties in the coating formulations or compositions.

The invention is also directed to a homogeneous, pourable liquid which improves properties in aqueous coatings, for example, improved water sensitivity. These improved properties are due to a reduction in the use level of the thickeners as described herein, needed to achieve a desired rheological profile.

The aqueous coating compositions of the invention typically include at least one latex polymer derived from at least one monomer, for example acrylic monomers. The at least one latex polymer in the aqueous coating composition can be a pure acrylic, a styrene acrylic, a vinyl acrylic or an acrylated ethylene vinyl acetate copolymer and is more preferably a pure acrylic. The at least one latex polymer is preferably derived from at least one acrylic monomer selected from the group consisting of acrylic acid, acrylic acid esters, methacrylic acid, and methacrylic acid esters. For example, the at least one latex polymer can be a butyl acrylate/methyl methacrylate copolymer or a 2-ethylhexyl acrylate/methyl methacrylate copolymer. Typically, the at least one latex polymer is further derived from one or more monomers selected from the group consisting of styrene, alpha-methyl styrene, vinyl chloride, acrylonitrile, methacrylonitrile, ureido methacrylate, vinyl acetate, vinyl esters of branched tertiary monocarboxylic acids, itaconic acid, crotonic acid, maleic acid, fumaric acid, ethylene, and $C_4$-$C_8$ conjugated dienes.

Latex paint formulations typically comprise additives, e.g., at least one pigment. In a preferred embodiment of the invention the latex paint formulation includes at least one pigment selected from the group consisting of TiO2, CaCO3, clay, aluminum oxide, silicon dioxide, magnesium oxide, sodium oxide, potassium oxide, talc, barytes, zinc oxide, zinc sulfite and mixtures thereof. More preferably the at least one pigment includes TiO2, calcium carbonate or clay.

In addition to the above components, the aqueous coating composition can include one or more additives selected from the group consisting of dispersants, surfactants, rheology modifiers, defoamers, thickeners, biocides, mildewcides, colorants, waxes, perfumes and co-solvents.

Compositions of the present invention may have an absence of one or more of anionic surfactant, cationic surfactant, nonionic surfactant, zwitterionic surfactant, and/or amphoteric surfactant.

These and other features and advantages of the present invention will become more readily apparent to those skilled in the art upon consideration of the following detailed description, which describe both the preferred and alternative embodiments of the present invention.

DETAILED DESCRIPTION OF THE PREFERRED EMBODIMENTS

The present invention relates to, in one embodiment, the use of a particular family of HASE copolymers for latex dispersions, binders, paints and coatings. Described herein are aqueous compositions, for example, aqueous coating compositions. The aqueous compositions of the invention are aqueous polymer dispersions which include at least one latex polymer. Paints or other aqueous coatings of the present invention typically further include at least one pigment. In another embodiment, the latex has a Tg of less than 30° C., more typically less than 20° C., still more typically in the range from 10 to −10° C., e.g., 0° C. In one embodiment, the latex has a Tg of less than 10° C., more typically less than 5° C., still more typically in the range from 5 to −10° C., e.g., 0° C.

As used herein, the term "alkyl" means a monovalent straight or branched saturated hydrocarbon radical, more typically, a monovalent straight or branched saturated ($C_1$-$C_{40}$) hydrocarbon radical, such as, for example, methyl, ethyl, n-propyl, isopropyl, n-butyl, isobutyl, tert-butyl, hexyl, octyl, hexadecyl, octadecyl, eicosyl, behenyl, tricontyl, and tetracontyl.

As used herein, the term "alkenyl" means an unsaturated straight or branched hydrocarbon radical, more typically an unsaturated straight, branched, ($C_2$-$C_{22}$) hydrocarbon radical, that contains one or more carbon-carbon double bonds, such as, for example, ethenyl, n-propenyl, iso-propenyl.

As used herein, the term "alkoxyl" means an oxy radical that is substituted with an alkyl group, such as for example, methoxyl, ethoxyl, propoxyl, isopropoxyl, or butoxyl, which may optionally be further substituted on one or more of the carbon atoms of the radical.

As used herein, the term "alkoxyalkyl" means an alkyl radical that is substituted with one or more alkoxy substituents, more typically a ($C_1$-$C_{22}$)alkyloxy-($C_1$-$C_6$)alkyl radical, such as methoxymethyl, and ethoxybutyl.

As used herein, terms "aqueous medium" and "aqueous media" are used herein to refer to any liquid medium of which water is a major component. Thus, the term includes water per se as well as aqueous solutions and dispersions.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkoxyl, alkenyl, halo, haloalkyl, monocyclic aryl, or amino, such as, for example, phenyl, methylphenyl, methoxyphenyl, dimethylphenyl, trimethylphenyl, chlorophenyl, trichloromethylphenyl, triisobutyl phenyl, tristyrylphenyl, and aminophenyl.

As used herein, the term "arylalkyl" means an alkyl group substituted with one or more aryl groups, more typically a ($C_1$-$C_{18}$)alkyl substituted with one or more ($C_6$-$C_{14}$)aryl substituents, such as, for example, phenylmethyl, phenylethyl, and triphenylmethyl.

As used herein, the term "aryloxy" means an oxy radical substituted with an aryl group, such as for example, phenyloxy, methylphenyl oxy, isopropylmethylphenyloxy.

As used herein, the terminology "($C_x$-$C_y$)" in reference to an organic group, wherein x and y are each integers, indicates that the group may contain from x carbon atoms to y carbon atoms per group.

As used herein, the term "cycloalkenyl" means an unsaturated hydrocarbon radical, typically an unsaturated ($C_5$-$C_{22}$) hydrocarbon radical, that contains one or more cyclic alkenyl rings and which may optionally be substituted on one or more carbon atoms of the ring with one or two ($C_1$-$C_6$) alkyl groups per carbon atom, such as cyclohexenyl, cycloheptenyl, and "bicycloalkenyl" means a cycloalkenyl ring system that comprises two condensed rings, such as bicycloheptenyl.

As used herein, the term "cycloalkyl" means a saturated hydrocarbon radical, more typically a saturated ($C_5$-$C_{22}$) hydrocarbon radical, that includes one or more cyclic alkyl rings, which may optionally be substituted on one or more carbon atoms of the ring with one or two ($C_1$-$C_6$)alkyl groups per carbon atom, such as, for example, cyclopentyl, cycloheptyl, cyclooctyl, and "bicyloalkyl" means a cycloalkyl ring system that comprises two condensed rings, such as bicycloheptyl.

As used herein, an indication that a composition is "free" of a specific material means the composition contains no measurable amount of that material.

As used herein, the term "heterocyclic" means a saturated or unsaturated organic radical that comprises a ring or condensed ring system, typically comprising from 4 to 16 ring atoms per ring or ring system, wherein such ring atoms comprise carbon atoms and at least one heteroatom, such as for example, O, N, S, or P per ring or ring system, which may optionally be substituted on one or more of the ring atoms, such as, for example, thiophenyl, benzothiphenyl, thianthrenyl, pyranyl, benzofuranyl, xanthenyl, pyrolidinyl, pyrrolyl, pyradinyl, pyrazinyl, pyrimadinyl, pyridazinyl, indolyl, quinonyl, carbazolyl, phenathrolinyl, thiazolyl, oxazolyl, phenoxazinyl, or phosphabenzenyl.

As used herein, the term "hydroxyalkyl" means an alkyl radical, more typically a ($C_1$-$C_{22}$)alkyl radical, that is substituted with one or more hydroxyl groups, such as for example, hydroxymethyl, hydroxyethyl, hydroxypropyl, and hydroxydecyl.

As used herein the term "(meth)acrylate" refers collectively and alternatively to the acrylate and methacrylate and the term "(meth)acrylamide" refers collectively and alternatively to the acrylamide and methacrylamide, so that, for example, "butyl (meth)acrylate" means butyl acrylate and/or butyl methacrylate.

As used herein, "molecular weight" in reference to a polymer or any portion thereof, means to the weight-average molecular weight ("$M_w$") of the polymer or portion. $M_w$ of a polymer is a value measured by gel permeation chromatography (GPC) with an aqueous eluent or an organic eluent (for example dimethylacetamide, dimethylformamide, and the like), depending on the composition of the polymer, light scattering (DLS or alternatively MALLS), viscometry, or a number of other standard techniques. $M_w$ of a portion of a polymer is a value calculated according to known techniques from the amounts of monomers, polymers, initiators and/or transfer agents used to make the portion.

In one embodiment, the copolymers for use in the present invention exhibit a weight average molecular weight, as determined by gel permeation chromatography (GPC) and light scattering of a solution of the polymer in tetrahydrofuran and compared to a polystyrene standard, of greater than or equal to 30,000 grams per mole ("g/mole"). HASE thickeners may not fully dissolve in THF but after hydrolysis they can dissolve in water and measurement can be run in a water gel permeation chromatography (GPC). Reference: Macromolecules 2000, 33, 2480. For example in a range of 30,000 to 2,000,000 g/mole.

As used herein, the indication that a radical may be "optionally substituted" or "optionally further substituted" means, in general, unless further limited either explicitly or by the context of such reference, such radical may be substituted with one or more inorganic or organic substituent groups, for example, alkyl, alkenyl, aryl, arylalkyl, alkaryl, a hetero atom, or heterocyclyl, or with one or more functional groups capable of coordinating to metal ions, such as hydroxyl, carbonyl, carboxyl, amino, imino, amido, phosphonic acid, sulphonic acid, or arsenate, or inorganic and organic esters thereof, such as, for example, sulphate or phosphate, or salts thereof.

As used herein, "parts by weight" or "pbw" in reference to a named compound refers to the amount of the named compound, exclusive, for example, of any associated solvent. In some instances, the trade name of the commercial source of the compound is also given, typically in parentheses. For example, a reference to "10 pbw cocoamidopropylbetaine ("CAPB", as MIRATAINE BET C-30)" means 10 pbw of the actual betaine compound, added in the form of a commercially available aqueous solution of the betaine compound having the trade name "MIRATAINE BET C-30", and exclusive of the water contained in the aqueous solution.

As used herein, an indication that a composition is "substantially free" of a specific material, means the composition contains no more than an insubstantial amount of that material, and an "insubstantial amount" means an amount that does not measurably affect the desired properties of the composition.

As used herein, the term "surfactant" means a compound that reduces surface tension when dissolved in water.

"Surfactant effective amount" means the amount of the surfactant that provides a surfactant effect to enhance the stability of emulsions of the polymers.

In one embodiment, described herein are pH responsive copolymers of a mixture of unsaturated copolymerizable monomers. In one embodiment, these pH responsive copolymers are substantially insoluble in water at a low pH. However, at higher pH they become swellable or soluble in water and thus exhibit thickening behavior. Thus, the pH responsive copolymer is interchangeably termed alkali swellable copolymer or alkali soluble copolymer. Typically the pH responsive copolymer is termed an alkali-soluble emulsion (ASE) copolymer and/or a hydrophobically modified alkali-soluble emulsion (HASE) copolymer. Although this copolymer is described as ASE and/or HASE copolymer it is not necessary to make a copolymer of this structure by emulsion polymerization. The copolymer may also be made by solution polymerization and comes within the invention whether made by emulsion polymerization or solution polymerization.

In one embodiment, the copolymer comprises a chain of monomeric units. In a further embodiment, the copolymer is an ASE and/or HASE copolymer. The polymer is a macromolecule having a relatively high molecular mass that comprises chains of multiple repetitions of the monomeric units, which are derived, actually or conceptually, from molecules of relatively low molecular mass and are connected to form a linear, branched, or network structure. The copolymer typically has a linear or branched structure, more typically single strand linear or branched structure. In one embodiment, a polymer having a predominantly single strand linear or branched structure is lightly crosslinked to form a polymer network having a low density of crosslinks. As used herein the term "single strand" in regard to a polymer means monomeric units of the polymer are connected such that adjacent monomeric units are joined to each other through two atoms, one on each of the adjacent monomeric units.

The copolymer may typically be regarded as having a "backbone", or main polymer chain, from which all branches and substituent groups of the polymer may be regarded as being pendant. Where two or more chains of the copolymer could equally be considered to be the main chain of the polymer, that chain is selected as the main chain which leads to the simplest representation of the polymer molecule. The monomeric units of the copolymer may be arranged in random, alternating, tapered, or block sequence along the copolymer chain.

The ASE and/or HASE copolymer typically has a weight average molecular weight of greater than or equal to about 30,000 grams per mole, typically the copolymer has a weight average molecular weight of greater than or equal to about 30,000 to 1,000,000 grams per mole or 30,000 to 500,000 grams per mole or 50,000 to 500,000 grams per mole.

The polymer of the present invention, in one embodiment, further comprises one or more acidic monomeric units, each independently comprising at least one acid group per acidic monomeric unit.

In one embodiment, the acidic monomeric units each independently comprise, per monomeric unit, at least one group according to structure (B.I):

wherein
$R^{31}$ is a moiety that comprises at least one carboxylic acid, sulfonic acid, or phosphoric acid group, and
$R^{32}$ is absent or is a bivalent linking group.

In one embodiment, $R^{32}$ is O, $-(CH_2)_n-O-$, or is according to structure (structure (B.II):

wherein:
n is an integer of from 1 to 6,
A is O or $NR^{17}$, and
$R^{17}$ is H or $(C_1-C_4)$alkyl.

In one embodiment, the one or more acidic monomeric units each independently comprise one or two carboxy groups per monomeric unit and may, if the acidic monomeric unit comprises a single carboxy group, further comprise an ester group according to $-CH_2COOR^{33}$, wherein $R^{33}$ is alkyl, more typically, $(C_1-C_6)$alkyl.

The acidic monomeric units may be made by known synthetic techniques, such as, for example, by grafting of one or more groups according to structure (B.I) onto a polymer backbone, such as a hydrocarbon polymer backbone, a polyester polymer backbone, or a polysaccharide polymer backbone. In the alternative, they may be made by polymerizing a monomer that comprises a reactive functional group and at least one group according to structure (B.I) per molecule.

In one embodiment the acidic monomer comprises one or more ethylenically unsaturated monocarboxylic acid monomers according to structure (B.III):

wherein:
$R^{31}$ and $R^{32}$ are each as described above, and
$R^{34}$ is a moiety having a site of ethylenic unsaturation.

In one embodiment, $R^{34}$ is a α-, β-unsaturated carbonyl compound. In one embodiment, $R^{34}$ is according to structure (B.IV):

wherein $R^{19}$ is H or $(C_1-C_4)$alkyl.

Suitable acidic monomers include, for example, ethylenically unsaturated carboxylic acid monomers, such as acrylic acid and methacrylic acid, ethylenically unsaturated dicarboxylic acid monomers, such as maleic acid and fumaric acid, ethylenically unsaturated alkyl monoesters of dicarboxylic acid monomers, such as butyl methyl maleate, ethylenically unsaturated sulphonic acid monomers, such as vinyl sulfonic acid 2-acrylamido-2-methylpropane sulfonic acid, and styrene sulfonic acid, and ethylenically unsaturated phosphonic acid monomers, such as vinyl phosphonic acid and allyl phosphonic acid, salts of any thereof, and mixtures of any thereof. Alternatively, corresponding ethylenically unsaturated anhydride or acid chloride monomers, such as maleic anhydride, may be used and subsequently hydrolyzed to give a pendant moiety having two acid groups. The preferred acidic monomeric units are derived from one or more monomers selected from acrylic acid, methacrylic acid, and mixtures thereof. Methacrylic acid has the following formula B. V:

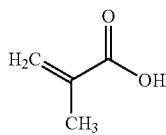

In one embodiment, the polymer of the present invention further comprises one or more nonionic monomeric units.

In one embodiment, the nonionic monomeric units each independently comprise, per monomeric unit, at least one group according to structure (0.1):

-$R^{42}$-$R^{41}$ (C.I)

wherein
$R^{41}$ is alkyl, hydroxyalkyl, alkoxyalkyl, cycloalkyl, aryl, arylalkyl, or aryloxy, and
$R^{42}$ is absent or is a bivalent linking group.

In one embodiment, $R^{41}$ is $(C_1-C_{22})$alkyl, $(C_1-C_{22})$hydroxyalkyl, $(C_2-C_{22})$alkoxyalkyl, $(C_6-C_{24})$cycloalkyl, $(C_6-C_{40})$aryl, or $(C_7-C_{40})$arylalkyl, more typically $(C_2-C_{12})$alkyl.

In one embodiment, $R^{41}$ is $(C_1-C_{22})$alkyl, more typically, $(C_1-C_{12})$alkyl.

In one embodiment, $R^{42}$ is O, —$(CH_2)_n$—O—, wherein n is an integer of from 1 to 6, or is according to structure (C.II):

wherein:
n is an integer of from 1 to 6,
A is O or $NR^{17}$, and
$R^{17}$ is H or $(C_1-C_4)$alkyl.

The nonionic monomeric units may be made by known synthetic techniques, such as, for example, by grafting of one or more groups onto a polymer backbone, such as a hydrocarbon polymer backbone, a polyester polymer backbone, or a polysaccharide polymer backbone, or a backbone made by polymerization, with, for example, the above described acidic, and hydrophobic monomers and copolymerizable with the first, second, and third monomers. Alternatively, the nonionic monomeric units may simply be non-grafted portions of a polymer backbone.

In one embodiment, the nonionic monomeric units are derived from a nonionic monomer, for example, ethyl acrylate, that comprises a reactive functional group, and is copolymerizable with the acidic monomers and hydrophobic monomers as described herein.

In one embodiment, the reactive functional group of the nonionic monomer is an ethylenically unsaturated group and the nonionic monomer is an ethylenically unsaturated monomer comprising at least one site of ethylenic unsaturation, more typically, an α-, β-unsaturated carbonyl moiety and at least one other group.

In one embodiment, the nonionic monomer comprises one or more compounds according to structure (C.III):

wherein:
$R^{41}$ and $R^{42}$ are each as described above, and
$R^{43}$ is a moiety having a site of ethylenic unsaturation.

In one embodiment, the compound according to structure (C.III) is an α-, β-unsaturated carbonyl compound. In one embodiment, $R^{43}$ is according to structure (C.IV):

wherein $R^{19}$ is H or $(C_1-C_4)$alkyl.

Suitable nonionic monomers include unsaturated monomers containing at least one group according to structure C.XXIII per molecule, including (meth)acrylic esters such as: methyl (meth)acrylate, ethyl (meth)acrylate, butyl (meth)acrylate, isobutyl (meth)acrylate, cyclohexyl (meth)acrylate, 2-ethylhexyl (meth)acrylate, isodecyl (meth)acrylate, lauryl (meth)acrylate isobornyl (meth)acrylate, benzyl (meth)acrylate, hydroxyethyl (meth)acrylate, hydroxypropyl (meth)acrylate, methoxyethyl (meth)acrylate, ethoxyethyl (meth)acrylate, phenoxyethyl (meth)acrylate, tetrahydrofurfuryl (meth)acrylate, glycidyl (meth)acrylate, dimethylaminoethyl (meth)acrylate, diethylaminoethyl (meth)acrylate, tert-butylaminoethyl (meth)acrylate, and acetoxyethyl (meth)acrylate, (meth)acrylamides such as, (meth)acrylamide, N-methylol (meth)acrylamide, N-butoxyethyl (meth)acrylamide, N,N-dimethyl (meth)acrylamide, N-isopropyl (meth) acrylamide, N-tert-butyl (meth)acrylamide, N-tert-octyl (meth)acrylamide, and diacetone (meth)acrylamide, vinyl esters such as vinyl acetate, vinyl propionate, vinyl 2-ethylhexanoate, N-vinylamides such as: N-vinylpyrrolidione, N-vinylcaprolactam, N-vinylformamide, and N-vinylacetamide, and vinyl ethers such as, methyl vinyl ether, ethyl vinyl ether, butyl vinyl ether, and hydroxybutyl vinyl ether, and ethylenically unsaturated aryl compounds, such as styrene.

In one embodiment, the HASE copolymer of the present invention is crosslinked. A crosslinked polymer can be made by, for example, reacting a mixture of hydrophobic, first acidic, and second acidic monomers with a nonionic monomer having more than one reactive functional group, such as for example, more than one site of ethylenic unsaturation per molecule. In one embodiment, the nonionic monomer comprises least one monomeric compound having more than one (meth)acrylic group per molecule, such as, for example, allyl methacrylate, ethylene glycol dimethacrylate, butylene glycol dimethacrylate, diallyl pentaerythritol, methylenebisacrylamide, pentaerythritol di-, tri- and tetra-acrylates, divinyl benzene, polyethylene glycol diacrylates, bisphenol A diacrylates, butanediol dimethacrylate, 2,2-dimethylpropanediol dimethacrylate, ethylene glycol dimethacrylate, phenylene diacrylate, or a mixture thereof.

Ethylene glycol dimethyl acrylate having the following formula

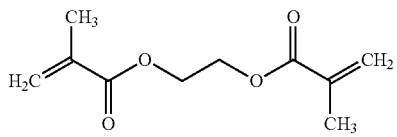

The pH responsive copolymer is made from a mixture of unsaturated copolymerizable monomers, wherein at least one is a novel monomer comprising, based on total weight of monomers:

A. about 0.1-70 weight percent, typically 0.5-50, 0.7-40, 1-40, 5-40, 5-30 or 10 to 40 weight percent, of at least one alpha beta-ethylenically unsaturated monomer according to structure D.XVI. In one embodiment, the novel monomer according to the present invention comprises, based on total weight of monomers: about 0.01 to 50 weight percent (wt %), or in another embodiment 0.05 to 30 weight percent, or in another embodiment 0.5 to 10 weight percent, or in another embodiment 1 to 10 weight percent, or in another embodiment 0.5 to 9 weight percent, or in another embodiment 0.5 to 7 weight percent, or in another embodiment 4 to 10 weight percent.

In one embodiment, the unsaturated monomer is an ethylenically unsaturated hydrophobic monomer comprising a compound according to structure D.XVI:

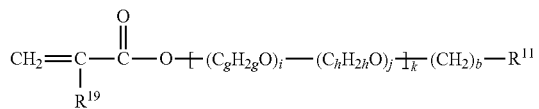

(D.XVI)

wherein:
g is an integer from 2 to 4;
h is an integer from 2 to 4;
b is an integer from 0 to 1;
k is an integer from 0 to 100, or from 0 to 25;
i is an integer from 0 to 40, or from 0 to 20;
j is an integer from 0 to 40, or from 0 to 20;
R19 is hydrogen; methyl or ethyl;
$R^{11}$ is a tri-substituted aromatic group according to the structure D.XII

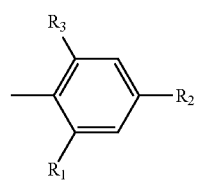

D.XII wherein $R_1$, $R_2$ and $R_3$ are independently selected from the following structures D.XIIa, D.XIIb, D.XIIc, D.XIId:

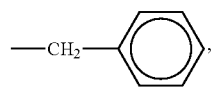

D.XIIIa

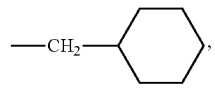

D.XIIIb

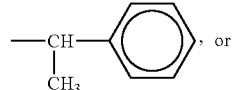

D.XIIIc

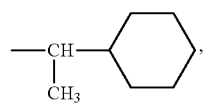

D.XIIId or a $C_2$-$C_{30}$ branched or linear alkyl group or alkenyl group; wherein at least one of $R_1$, $R_2$ and $R_3$ is the $C_2$-$C_{30}$ branched or linear alkyl group or alkenyl group and at least one of $R_1$, $R_2$ and $R_3$ is selected from structure D.XIIa, D.XIIb, D.XIIc, or D.XIId.

In one embodiment, the $C_2$-$C_{30}$ branched or linear alkyl group is a $C_3$-$C_{30}$ branched or linear alkyl group or alkenyl group. In one embodiment, the $C_2$-$C_{30}$ branched or linear alkyl group or alkenyl group is a $C_4$-$C_{30}$ branched or linear alkyl group or alkenyl group. In one embodiment, the $C_2$-$C_{30}$ branched or linear alkyl group or alkenyl group is a $C_5$-$C_{30}$ branched or linear alkyl group or alkenyl group. In one embodiment, the $C_2$-$C_{30}$ branched or linear alkyl group or alkenyl group is a $C_6$-$C_{30}$ branched or linear alkyl group or alkenyl group. In one embodiment, the $C_2$-$C_{30}$ branched or linear alkyl group or alkenyl group is a $C_7$-$C_{30}$ branched or linear alkyl group or alkenyl group. In one embodiment, the $C_2$-$C_{30}$ branched or linear alkyl group or alkenyl group is a $C_8$-$C_{30}$ branched or linear alkyl group or alkenyl group. In one embodiment, the $C_2$-$C_{30}$ branched or linear alkyl group or alkenyl group is a $C_9$-$C_{30}$ branched or linear alkyl group or alkenyl group. In one embodiment, the $C_2$-$C_{30}$ branched or linear alkyl group or alkenyl group is a $C_{10}$-$C_{30}$ branched or linear alkyl group or alkenyl group. In one embodiment, the $C_2$-$C_{30}$ branched or linear alkyl group is a $C_9$-$C_{14}$ branched or linear alkyl group or alkenyl group. In one embodiment, the $C_2$-$C_{30}$ branched or linear alkyl group is a $C_8$-$C_{12}$ branched or linear alkyl group or alkenyl group. In one embodiment, the $C_2$-$C_{30}$ branched or linear alkyl group is a $C_{23}$-$C_{30}$ branched or linear alkyl group or alkenyl group.

In another embodiment, the $C_2$-$C_{30}$ branched or linear alkyl group or alkenyl group is a $C_2$-$C_{28}$ branched or linear alkyl group or alkenyl group. In one embodiment, the $C_2$-$C_{30}$ branched or linear alkyl group or alkenyl group is a $C_3$-$C_{26}$ branched or linear alkyl group or alkenyl group. In one embodiment, the $C_2$-$C_{30}$ branched or linear alkyl group or alkenyl group is a $C_4$-$C_{24}$ branched or linear alkyl group or alkenyl group. In one embodiment, the $C_2$-$C_{30}$ branched or linear alkyl group or alkenyl group is a $C_6$-$C_{24}$ branched or linear alkyl group or alkenyl group. In another embodiment, the $C_8$-$C_{24}$ branched or linear alkyl group or alkenyl group is a $C_{10}$-$C_{24}$ branched or linear alkyl group or alkenyl group.

In another embodiment, the $C_2$-$C_{30}$ branched or linear alkyl group or alkenyl group is a $C_6$-$C_{20}$ branched or linear alkyl group or alkenyl group. In another embodiment, the $C_2$-$C_{30}$ branched or linear alkyl group or alkenyl group is a $C_6$-$C_{18}$ branched or linear alkyl group or alkenyl group. In another embodiment, the $C_2$-$C_{30}$ branched or linear alkyl group or alkenyl group is a $C_8$-$C_{16}$ branched or linear alkyl group or alkenyl group.

In another embodiment, at least one of $R_1$, $R_2$ and $R_3$ is a branched or linear alkyl group or alkenyl group having, as a lower limit, a $C_2$ linear alkyl group, or in another embodiment, a $C_3$ branched or linear alkyl group or alkenyl group, or in another embodiment, a $C_4$ branched or linear alkyl group or alkenyl group, or in a further embodiment, a $C_5$ branched or linear alkyl group or alkenyl group, or in another embodiment, a $C_6$ branched or linear alkyl group or alkenyl group, or in yet another embodiment, a $C_7$ branched or linear alkyl group or alkenyl group, or in another embodiment, a $C_8$ branched or linear alkyl group or alkenyl group, or in another embodiment, a $C_9$ branched or linear alkyl group or alkenyl group, or in another embodiment, a $C_{10}$ branched or linear alkyl group or alkenyl group, or in another embodiment, a $C_{12}$ branched or linear alkyl group or alkenyl group, or in another embodiment, a $C_{14}$ branched or linear alkyl group or alkenyl group, or in yet a further embodiment, a $C_{16}$ branched or linear alkyl group or alkenyl group.

In one embodiment, the unsaturated monomer is an ethylenically unsaturated hydrophobic monomer comprising a compound according to structure D.XXX:

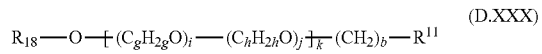
(D.XXX)

wherein:
g is an integer from 2 to 4;
h is an integer from 2 to 4;
b is an integer from 0 to 1;
k is an integer from 0 to 100;
i is an integer from 0 to 40, or from 0 to 20;
j is an integer from 0 to 40, or from 0 to 20;
$R^{18}$ is a moiety having a site of ethylenic unsaturation;
$R^{11}$ is a tri-substituted aromatic group according to the structure D.XII

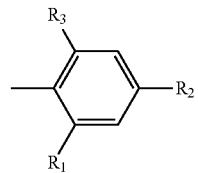
D.XII wherein $R_1$, $R_2$ and $R_3$ are independently selected from the following structures D.XIIa, D.XIIb, D.XIIc, D.XIId:

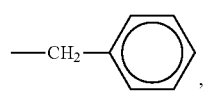
D.XIIIa

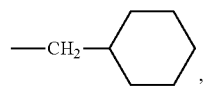
D.XIIIb

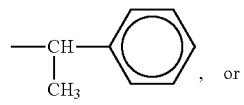
D.XIIIc

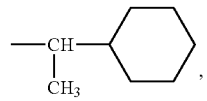
D.XIIId or a $C_2$-$C_{30}$ branched or linear alkyl group or alkenyl group; wherein at least one of $R_1$, $R_2$ and $R_3$ is the $C_2$-$C_{30}$ branched or linear alkyl group or alkenyl group and at least one of $R_1$, $R_2$ and $R_3$ is selected from structure D.XIIa, D.XIIb, D.XIIc, or D.XIId.

In one embodiment, $R^{18}$ is according to structure (D.XV):

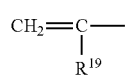
(D.XV)

wherein $R^{19}$ is H or $(C_1$-$C_4)$alkyl.

The $C_2$-$C_{30}$ branched or linear alkyl group or alkenyl group can be a $C_3$-$C_{14}$ branched or linear alkyl group or alkenyl group, or a $C_6$-$C_{14}$ branched or linear alkyl group or alkenyl group, or a $C_8$-$C_{12}$ branched or linear alkyl group or alkenyl group, or a $C_4$-$C_{12}$ branched or linear alkyl group or alkenyl group. Preferably, The $C_2$-$C_{30}$ branched or linear alkyl group or alkenyl group can be a $C_8$-$C_{12}$ branched or linear alkyl group or alkenyl group, or a $C_4$-$C_{12}$ branched or linear alkyl group or alkenyl group.

In one embodiment, the $C_2$-$C_{30}$ branched or linear alkyl group or alkenyl group is a $C_3$-$C_{30}$ branched or linear alkyl group or alkenyl group. In one embodiment, the $C_2$-$C_{30}$ branched or linear alkyl group or alkenyl group is a $C_4$-$C_{30}$ branched or linear alkyl group or alkenyl group. In one embodiment, the $C_2$-$C_{30}$ branched or linear alkyl group or alkenyl group is a $C_5$-$C_{30}$ branched or linear alkyl group or alkenyl group. In one embodiment, the $C_2$-$C_{30}$ branched or linear alkyl group or alkenyl group is a $C_6$-$C_{30}$ branched or linear alkyl group or alkenyl group. In one embodiment, the $C_2$-$C_{30}$ branched or linear alkyl group or alkenyl group is a $C_7$-$C_{30}$ branched or linear alkyl group or alkenyl group. In one embodiment, the $C_2$-$C_{30}$ branched or linear alkyl group or alkenyl group is a $C_8$-$C_{30}$ branched or linear alkyl group or alkenyl group. In one embodiment, the $C_2$-$C_{30}$ branched or linear alkyl group or alkenyl group is a $C_9$-$C_{30}$ branched or linear alkyl group or alkenyl group. In one embodiment, the $C_2$-$C_{30}$ branched or linear alkyl group or alkenyl group is a $C_{10}$-$C_{30}$ branched or linear alkyl group or alkenyl group.

In another embodiment, the $C_2$-$C_{30}$ branched or linear alkyl group or alkenyl group is a $C_2$-$C_{28}$ branched or linear alkyl group or alkenyl group. In one embodiment, the $C_2$-$C_{30}$ branched or linear alkyl group or alkenyl group is a $C_3$-$C_{26}$ branched or linear alkyl group or alkenyl group. In one embodiment, the $C_2$-$C_{30}$ branched or linear alkyl group or alkenyl group is a $C_4$-$C_{24}$ branched or linear alkyl group or alkenyl group. In one embodiment, the $C_2$-$C_{30}$ branched or linear alkyl group or alkenyl group is a $C_6$-$C_{24}$ branched or linear alkyl group or alkenyl group. In another embodiment, the $C_8$-$C_{24}$ branched or linear alkyl group or alkenyl group is a $C_{10}$-$C_{24}$ branched or linear alkyl group or alkenyl group.

In another embodiment, the $C_2$-$C_{30}$ branched or linear alkyl group or alkenyl group is a $C_6$-$C_{20}$ branched or linear alkyl group or alkenyl group. In another embodiment, the $C_2$-$C_{30}$ branched or linear alkyl group or alkenyl group is a $C_6$-$C_{18}$ branched or linear alkyl group or alkenyl group. In another embodiment, the $C_2$-$C_{30}$ branched or linear alkyl group or alkenyl group is a $C_8$-$C_{16}$ branched or linear alkyl group or alkenyl group.

In one embodiment, the $R^{11}$ is a tri-substituted aromatic group according to the structure D.XII

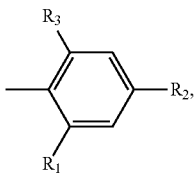

(D.XII)

wherein $R_1$, $R_2$ and $R_3$ are independently selected from:
a styryl group, or
a $C_2$-$C_{30}$ branched or linear alkyl group or alkenyl group;
wherein at least one of $R_1$, $R_2$ and $R_3$ is the $C_2$-$C_{30}$ branched or linear alkyl group or alkenyl group and at least one of $R_1$, $R_2$ and $R_3$ is the styryl group.

In another embodiment, the $R^{11}$ is a tri-substituted aromatic group is according to structure D.XII-1:

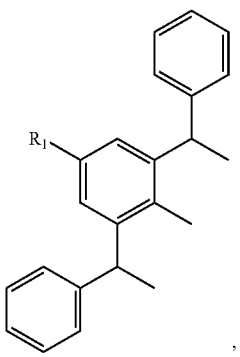

(D.XII-1)

wherein $R_1$, is the $C_2$-$C_{30}$ branched or linear alkyl group or alkenyl group In contrast to the ASE copolymers, the HASE copolymers further comprise hydrophobic monomeric units derived from a hydrophobic monomer. These hydrophobic monomers are ethylenically unsaturated hydrophobic monomers.

In one embodiment, the hydrophobic monomeric units each independently comprise a tri-substituted group according to structure (D.I):

—R$^{14}$-R$^{13}$-R$^{12}$-R$^{11}$ (D.I).

$R^{12}$ is absent or is a bivalent linking group,
$R^{13}$ is bivalent polyether group, and
$R^{14}$ is absent or is a bivalent linking group.
$R^{11}$ is according to structure (D.XII), above;

More typically, $R^{12}$ is O, a bivalent hydrocarbon group, even more typically a methylene group or chain of from 2 to 6 methylene units, or a bivalent alkyleneoxyl group, such as ethyleneoxy. In one embodiment, $R^{12}$ is according to structure (D.VIII):

—(CH$_2$)$_b$—A— (D.IX)

wherein A is O or absent, and b is an integer of from 1 to 6.

More typically, $R^{13}$ is a bivalent polyether group comprising a linear chain of from 2 to 100 units, each of which may independently be $(C_2$-$C_4)$oxyalkylene, more typically, $(C_2$-$C_3)$oxyalkylene. In one embodiment, $R^{13}$ is a bivalent polyether group comprising a chain of from 2 to 100 polymerized oxyethylene units and oxypropylene units, which may be arranged alternately, randomly, or in blocks. In one embodiment, $R^{13}$ is a bivalent polyether group comprising a block of polyoxyethylene units and a block of oxypropylene units, more typically, a block of polyoxyethylene units and a block of oxypropylene units, wherein the block of oxypropylene units is disposed between and links the block of oxyethylene units and the $R^{12}$ substituent, if present, or the $R^{11}$ substituent, if $R^{12}$ is not present.

In one embodiment, $R_{12}$ is —(CH$_2$)$_x$O—, wherein x is an integer from 1 to 20 (e.g., use of styrenated benzyl alcohols)

In another embodiment, $R_{12}$ is —CH$_2$CH(OH)CH$_2$O— or —CH$_2$CH(CH$_2$OH)O— (e.g., use of epichlorohydrin as coupling agent)

In one embodiment, $R_{13}$ is:
—[CH(R$_{20}$)CH(R$_{21}$)O]$_x$— wherein x is an integer of from 0 to 100, and $R_{20}$ and $R_{21}$ are independently selected from any of the following:
H; —CH$_2$OH; phenyl; —CH$_2$Cl;
a $C_1$-$C_{30}$ straight or branched alkyl or alkenyl;
—CH$_2$OR$_{22}$ wherein $R_{22}$ is $C_1$-$C_{30}$ straight or branched alkyl or alkenyl, phenyl, or alkyl substituted phenyl; or
R'COOCH$_2$— where R' is $C_1$-$C_{30}$ straight or branched alkyl or alkenyl.

In one embodiment, $R^{13}$ is according to structure (D.X):

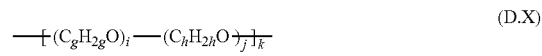

—[(C$_g$H$_{2g}$O)$_i$—(C$_h$H$_{2h}$O)$_j$]$_k$— (D.X)

wherein:
g and h are independently integers of from 2 to 5, more typically 2 or 3,
each i is independently an integer of from 1 to about 80, more typically from 1 to about 50,
each j is independently an integer of from 0 to about 80, more typically from 1 to about 50, k is an integer of from 1 to about 50, provided that the product obtained by multiplying the integer k times the sum of i+j is from 2 to about 100.

In another embodiment k is an integer having a lower limit of 0. In another embodiment k is an integer having a lower limit of 1. In another embodiment k is an integer having a lower limit of 3. In another embodiment k is an integer having a lower limit of 5. In another embodiment k is an integer having a lower limit of 8. In another embodiment k is an integer having a lower limit of 10. In another embodiment k is an integer having an upper limit of 100. In another embodiment k is an integer having an upper limit of 75. In another embodiment k is an integer having an upper limit of 50. In another embodiment k is an integer having an upper limit of 40. In another embodiment k is an integer having an upper limit of 60. In another embodiment k is an integer having an upper limit of 25. In another embodiment k is an integer having an upper limit of 35.

If i≠0, j≠0, and g≠h, the respective —($C_pH_{2p}O$)— and —($C_qH_{2q}O$)— oxylakylene units may be arranged randomly, in blocks, or in alternating order.

In one embodiment,
g=2,
h=3,
i is an integer of from 1 to 50, more typically 10 to 40, and even more typically from 15 to about 30,
j is an integer of from 1 to 30, more typically from 2 to 20, and even more typically from about 2 to about 10, and
k=1.

In one embodiment, $R^{14}$ is O, —$(CH_2)_n$—O—, or is according to structure (D.XI):

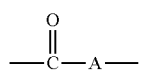

(D.XI)

wherein:
n is an integer of from 1 to 6,
A is O or $NR^{17}$, and
$R^{17}$ is H or ($C_1$-$C_4$)alkyl.

In another embodiment of structure (D.I) $R^{11}$ is a trisubstituted group according to the following structure D.XII.

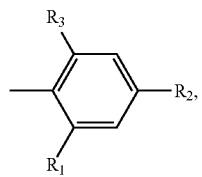

D.XII wherein $R_1$, $R_2$ and $R_3$ are independently selected from the following structures:

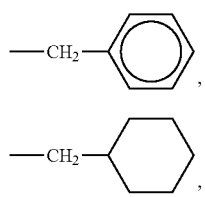

D.XIIIa

D.XIIIb

-continued

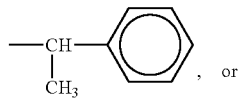

D.XIIIc

, or

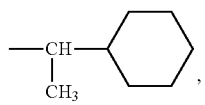

D.XIIId

, or a $C_2$-$C_{30}$ branched or linear alkyl group or alkenyl group.

In one embodiment, at least one of $R_1$, $R_2$ and $R_3$ is the $C_2$-$C_{30}$ branched or linear alkyl group or alkenyl group and at least one of $R_1$, $R_2$ and $R_3$ is selected from structure D.XIIa, D.XIIb, D.XIIc, or D.XIId.

The hydrophobic monomeric units may be made by known synthetic techniques, such as, for example, by grafting of one or more groups according to structure (D.I) onto a polymer backbone, such as a hydrocarbon polymer backbone, a polyester polymer backbone, or a polysaccharide polymer backbone, or by copolymerization, with, for example, the acidic monomer and nonionic monomer described above, of at least one other monomer selected from monomers that comprise a reactive functional group and at least one group according to structure (D.I) per molecule.

In one embodiment, the hydrophobic monomeric units are derived from at least one hydrophobic monomer selected from monomers that comprise a reactive functional group and at least one group according to structure (D.I) per molecule.

In one embodiment, the reactive functional group of the first monomer is an ethylenically unsaturated group. Thus, the hydrophobic monomer is selected from ethylenically unsaturated monomers that comprise at least one site of ethylenic unsaturation, more typically, an α-, β-unsaturated carbonyl moiety, and least one group according to structure (I) per molecule.

In one embodiment, the hydrophobic monomer comprises one or more compounds according to structure (D.XIV):

(D.XIV)

wherein:
$R^{11}$, $R^{12}$, $R^{13}$, and $R^{14}$ are each as described above, and
$R^{18}$ is a moiety having a site of ethylenic unsaturation.

In one embodiment, the compound according to structure (D.XI) is an α-, β-unsaturated carbonyl compound.

In one embodiment, $R^{18}$ is according to structure (D.XV):

(D.XV)

wherein $R^{19}$ is H or ($C_1$-$C_4$)alkyl.

In one embodiment, the hydrophobic monomer is selected from monomers according to structure (D.XVI):

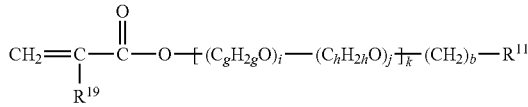

(D.XVI)

wherein:

$R^{11}$ is a tri-substituted group according to the above-discussed structure D.XII.
and
$R^{19}$, b, g, h, i, j, and k are each as defined above, namely:
$R^{19}$ is H or $(C_1-C_4)$alkyl,
b is an integer of from 1 to 6,
g and h are independently integers of from 2 to 5, more typically 2 or 3,
each i is independently an integer of from 1 to about 80, more typically from 1 to about 50,
each j is independently an integer of from 0 to about 80, more typically from 1 to about 50,
k is an integer of from 1 to about 50, provided that the product obtained by multiplying the integer k times the sum of i+j is from 2 to about 100.

In another embodiment k is an integer having a lower limit of 0. In another embodiment k is an integer having a lower limit of 1. In another embodiment k is an integer having a lower limit of 3. In another embodiment k is an integer having a lower limit of 5. In another embodiment k is an integer having a lower limit of 8. In another embodiment k is an integer having a lower limit of 10. In another embodiment k is an integer having an upper limit of 100. In another embodiment k is an integer having an upper limit of 75. In another embodiment k is an integer having an upper limit of 50. In another embodiment k is an integer having an upper limit of 40. In another embodiment k is an integer having an upper limit of 60. In another embodiment k is an integer having an upper limit of 25. In another embodiment k is an integer having an upper limit of 35.

In another embodiment of monomers according to structure (D.XVI) $R^{11}$ is a tri-substituted group according to the following structure D.XII and $R^{19}$, b, g, h, i, j, and k are each as defined above. An example of a suitable monomer has structure D.XVia:

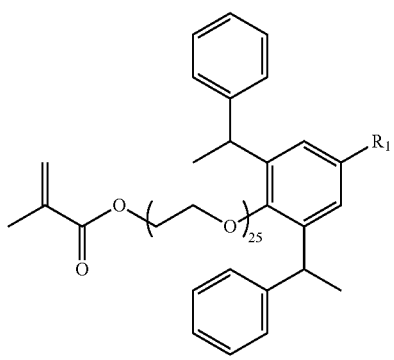

D.XVIa

Wherein $R_1$, $R_2$ and $R_3$ is a $C_2-C_{30}$ branched or linear alkyl group or alkenyl group, typically a $C_4-C_{12}$ branched or linear alkyl group or alkenyl group or a $C_8-C_{12}$ branched or linear alkyl group or alkenyl group.

The hydrophobic monomeric units may be made by known synthetic techniques, for example, by grafting of one or more groups according to structure D.XVII onto a polymer backbone, such as a hydrocarbon polymer backbone, a polyester polymer backbone, or a polysaccharide polymer backbone, or by copolymerization, with, for example, the above-described acidic monomer and the nonionic monomer described above.

In one embodiment, the hydrophobic monomeric units are derived from copolymerizing at least one monomer that comprises a reactive functional group and at least one group according to structure (D.XXI) per molecule.

In one embodiment, the reactive group of the hydrophobic monomer is an ethylenically unsaturated group and the second monomer is an ethylenically unsaturated monomer comprises at least one site of ethylenic unsaturation, more typically, an α-, β-unsaturated carbonyl moiety, and at least one group according to structure (D.XXI) per molecule and copolymerizable with the first monomer.

In one embodiment wherein the nonionic ethylenically unsaturated hydrophobic monomer comprises a compound according to: structure D.XXVIIa, structure D.XXVIIb, structure D.XXVIIc or structure D.XXVIId

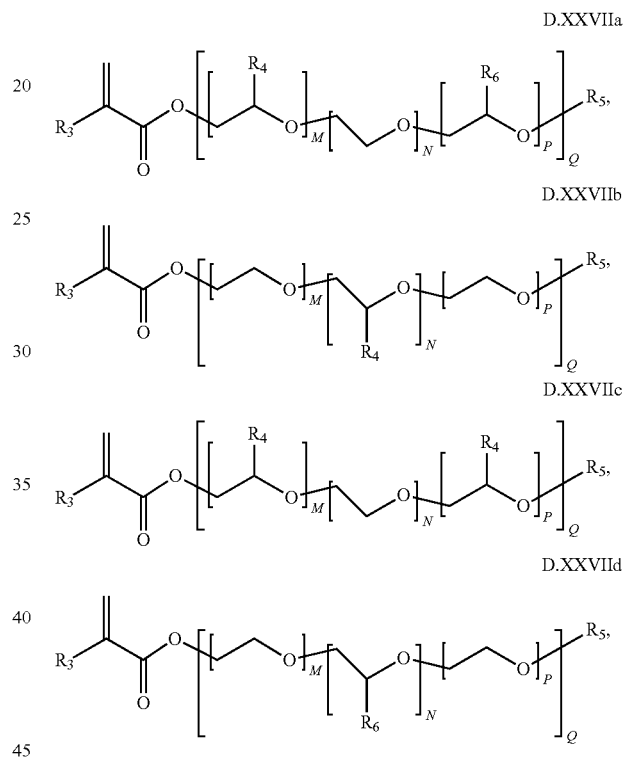

wherein $R_3$ is H or $CH_3$; $R_4$ is independently an alkyl chain containing 1 to about 4 carbon atoms; $R_6$ is an alkyl chain containing 1 to about 4 carbon atoms; M is an integer from 0 to about 50 (preferably about 1 to 50, more preferably about 5 to 30); N is an integer from 0 to 20 (preferably 1 to 20, more preferably 5 to 15); P is an integer from 0 to about 50 (preferably 0 to 30); wherein P+M is greater than or equal to 1; wherein Q is an integer from 1 to 4 (typically 1 to 2). $R_5$ is a tri-substituted group according to the following structure D.XII.

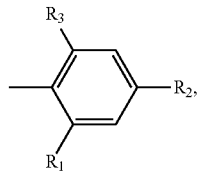

D.XII wherein $R_1$, $R_2$ and $R_3$ are independently selected from the following structures:

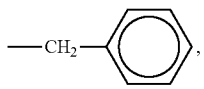 D.XIIIa

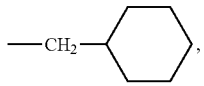 D.XIIIb

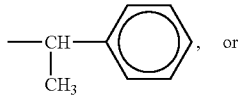 D.XIIIc

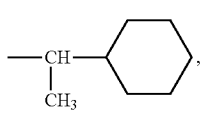 D.XIIId or a $C_2$-$C_{30}$ branched or linear alkyl group or alkenyl group.

In one embodiment, at least one of $R_1$, $R_2$ and $R_3$ is the $C_2$-$C_{30}$ branched or linear alkyl group and at least one of $R_1$, $R_2$ and $R_3$ is selected from structure D.XIIa, D.XIIb, D.XIIc, or D.XIId.

Making the ASE and/or HASE Copolymer

The pH responsive copolymer is the product of copolymerization of a mixture of monomers, comprising:

A. about 0-60 weight percent, preferably 5 to 30 weight percent, of at least one C3-C8 alpha beta-ethylenically unsaturated acidic monomer, preferably a C3-C8 alpha beta-ethylenically unsaturated carboxylic acid monomer;

B. about 15-70 weight percent, typically 20 to 50 weight percent, of at least one non-ionic, copolymerizable C2-C12 alpha, beta-ethylenically unsaturated monomer.

C. about 0.01 to 30 weight percent, preferably 0.05 to 30 weight percent or typically 5 to 20 weight percent, of at least one non-ionic ethylenically unsaturated hydrophobic monomer.

The pH responsive copolymer of the present invention can be conveniently prepared from the above-described monomers by known aqueous emulsion polymerization techniques using free-radical producing initiators, typically in an amount from 0.01 percent to 3 percent, based on the weight of the monomers.

In one embodiment, the polymerization is conducted at a pH of about 5.0 or less. Polymerization at an acid pH of about 5.0 or less permits direct preparation of an aqueous colloidal dispersion having relatively high solids content without the problem of excessive viscosity.

In one embodiment, the polymerization is conducted in the presence of one or more free-radical producing initiators selected from peroxygen compounds. Useful peroxygen compounds include inorganic persulfate compounds such as ammonium persulfate, potassium persulfate, sodium persulfate, peroxides such as hydrogen peroxide, organic hydroperoxides, for example, cumene hydroperoxide, and t-butyl hydroperoxide, organic peroxides, for example, benzoyl peroxide, acetyl peroxide, lauroyl peroxide, peracetic acid, and perbenzoic acid (sometimes activated by a water-soluble reducing agent such as ferrous compound or sodium bisulfite), and other free-radical producing materials or techniques such as 2,2'-azobisisobutyronitrile and high energy radiation sources.

In one embodiment, the polymerization is conducted in the presence of one or more emulsifiers. Useful emulsifiers include anionic surfactants, nonionic surfactants, amphoteric surfactants, and zwitterionic surfactants. In one embodiment, the emulsion polymerization is conducted in the presence of one or more anionic surfactants. Examples of anionic emulsifiers are the alkali metal alkyl aryl sulfonates, the alkali metal alkyl sulfates and the sulfonated alkyl esters. Specific examples of these well-known emulsifiers are sodium dodecyl benzene sulfonate, sodium dodecyl butylnaphthalene sulfonate, sodium lauryl sulfate, disodium dodecyl diphenyl ether disulfonate, disodium n-octadecyl sulfosuccinamate and sodium dioctyl sulfosuccinate. Known nonionic emulsifiers include, for example, fatty alcohols, alkoxylated fatty alcohols, and alkylpolyglucosides.

The emulsion polymerization may, optionally, be conducted in the presence, in an amount up to about 10 parts per 100 parts of polymerizable monomers, of one or more chain transfer agents. Representative chain transfer agents are carbon tetrachloride, bromoform, bromotrichloromethane, and long-chain alkyl mercaptans and thioesters, such as n-dodecyl mercaptan, t-dodecyl mercaptan, octyl mercaptan, tetradecyl mercaptan, hexadecyl mercaptan, butyl thioglycolate, isooctyl thioglycolate, and dodecyl thioglycolate.

Optionally, other ingredients well known in the emulsion polymerization art may be included, such as chelating agents, buffering agents, inorganic salts and pH adjusting agents.

In one embodiment, the polymerization is carried out at a temperature between about 60° C. and 90° C., but higher or lower temperatures may be used. The polymerization can be conducted batchwise, stepwise, or continuously with batch and/or continuous addition of the monomers, in a conventional manner.

The monomers can be copolymerized in such proportions, and the resulting emulsion polymers can be physically blended, to give products with the desired balance of properties for specific applications. For example, for analogous polymers of a given molecular weight, increasing the amount of first monomer tends to increase the yield strength exhibited by the polymer, increasing the relative amount of second monomer tends to increase the viscosity of the polymer. One or more fourth monomers may be added to adjust the properties of the polymer.

These polymeric products prepared by emulsion polymerization at an acid pH are in the form of stable aqueous colloidal dispersions containing the polymer dispersed as discrete particles having average particle diameters of about 400 to about 3000 Å (40 to 300 nanometers) and preferably about 600 to about 1750 Å (60 to 175 nanometers), as measured by light scattering. Dispersions containing polymer particles smaller than about 400 Å (40 nanometers) are difficult to stabilize, while particles larger than about 3000 Å (300 nanometers) reduce the ease of dispersion in the aqueous products to be thickened.

In one embodiment, the polymer composition is in the form of an aqueous polymer dispersion, typically having a solids content including the polymer and any surfactants that may be present and based on the total weight of the polymer dispersion, of up to about 60 wt % and, more typically about 20 to about 50 wt %.

Alternatively this (co)polymerization may also be conducted by different methods or in different solvents. The scope of methods and solvents is well known to those skilled in the art.

Thus, these polymers for use in the present invention can be made using known solution polymerization techniques, wherein the reactant monomers and initiator are dissolved in an appropriate solvent such as toluene, xylene, tetrahydrofuran, or mixtures thereof. Polymerization can be accomplished in the time and at the temperature necessary, e.g., 60° C. to 80° C. and about 2 to 24 hours. The polymer product can be isolated through normal separation techniques, including solvent stripping.

In one embodiment, these polymers for use in the present invention exhibit a weight average molecular weight, as determined by gel permeation chromatography and light scattering of a solution of the polymer in tetrahydrofuran and compared to a polystyrene standard, of greater than or equal to 30,000 grams per mole ("g/mole"). HASE thickeners may not fully dissolve in THF but after hydrolysis they can dissolve in water and measurement can be run in a water gel permeation chromatography (GPC). Reference: Macromolecules 2000, 33, 2480. For example in a range of 30,000 to 5,000,000 g/mole. More typically the polymer of the present invention exhibits a weight average molecular weight of from about 100,000 g/mole, and even more typically from about 150,000 g/mole, to about 1,500,000 g/mole, more typically to about 1,000,000 g/mole, and even more typically to about 800,000 g/mole.

In one embodiment, these pH responsive copolymers for use in the present invention are in the form of an aqueous colloidal polymer dispersion. When the polymer composition is in the form of an aqueous colloidal polymer dispersion, the composition is maintained at a pH of about 5 or less to maintain stability. More typically, the aqueous colloidal polymer dispersion composition has a pH of about 1.5 to about 3. When thickening of the composition is desired, the pH of the composition can be increased to a value above about 5 by addition of a base to solubilize the polymer.

These ASE and HASE copolymers and compositions for use as thickeners in the present invention are pH-responsive. At the lower pH levels at which the emulsion polymerization takes place, i.e., pH levels of 5 or less, the composition is relatively thin or non-viscous. When the pH of the copolymer dispersion is neutralized or adjusted by addition of a base to a pH of about 5.5 or more, preferably about 6 to about 11, the composition thickens substantially. The composition turns from semi-opaque or opaque to translucent or transparent as viscosity increases. Viscosity increases as copolymer dissolves partially or completely in the aqueous phase of the composition. Neutralization can occur in situ when the emulsion copolymer is blended with the base and added to the aqueous phase. Or, if desired for a given application, neutralization can be carried out when blending with an aqueous product. Useful bases include, but are not limited to, ammonium hydroxide, an amine, sodium hydroxide, potassium carbonate or the like.

For example, the HASE copolymer having a polymer backbone including MAA and EA is a pH-sensitive thickener. Typically the copolymer is a latex at pH=2.3. When neutralized with a suitable base to a pH above about 5.5, the carboxyl groups on the methacrylic acid ionize to carboxylate ions. The charge on the polymer induces a conformational change, and the white latex becomes water-soluble, thus increasing the hydrodynamic volume of the polymer. When the HASE copolymers swell, the pendant hydrophobic groups are free to build associations with one another and with other hydrophobes available in the formulation, such as surfactants, particulates, emulsion droplets and dyes. This phenomenon creates a network structure that results in a significant viscosity build.

IV. Uses of the pH Responsive Polymer

The polymers and polymer compositions according to the present invention are useful as water-soluble thickeners for a wide variety of applications ranging from home care, personal care and oilfield drilling fluids. They are particularly useful for aqueous paints and coatings. Solution-polymerized polymers can be used in solvent systems or emulsified by known techniques for use in aqueous systems. Other uses include latexes and detergents. Useful cosmetic compositions will typically have an aqueous carrier, a pigment and/or cosmetic active, a HASE emulsion polymer, and optional adjuvants. Useful detergents and cleansers will typically have aqueous carrier, a HASE emulsion polymer, and optional adjuvants. Oilfield drilling fluids will typically have an aqueous carrier, HASE emulsion polymer as a thickener/viscosity modifier, and optional adjuvants. The oilfield drilling fluids are injected into the oilfield formation. Useful latex coatings will typically have an aqueous carrier, a HASE emulsion polymer, and optional adjuvants.

The HASE emulsion polymers according to the present invention as described herein are particularly useful as thickeners for a wide variety of water-based compositions. Such compositions include brine, slurries, and colloidal dispersions of water-insoluble inorganic and organic materials, such as natural rubber, synthetic or artificial latexes. The emulsion polymers of the invention are especially useful in areas requiring thickening at neutral pHs, such as in cosmetics.

In one embodiment, the aqueous composition comprising the pH responsive polymer of the present invention exhibits viscoelastic properties at neutral to alkaline pH values, typically at pH values greater than or equal to about 5, more typically greater than or equal to about 5.5, even more typically from about 6 to about 9.

IV. Use of the pH Responsive Polymer with Binders which are Latex Polymers

Embodiments of the invention, such as latex paint, may contain more than one category of latex. There can be a first latex namely, the HASE copolymer, as a thickener. There can also be a second latex, for example RHOPLEX SG30 or REVACRYL synthetic latex emulsion resins, as a binder for latex paint.

Synthetic latexes take the form of aqueous dispersions/suspensions of particles of latex polymers. Synthetic latexes include aqueous colloidal dispersions of water-insoluble polymers prepared by emulsion polymerization of one or more ethylenically unsaturated monomers. Typical of such synthetic latexes are emulsion copolymers of monoethylenically unsaturated compounds, such as styrene, methyl methacrylate, acrylonitrile with a conjugated diolefin, such as butadiene or isoprene; copolymers of styrene, acrylic and methacrylic esters, copolymers of vinyl halide, vinylidene halide, vinyl acetate and the like. Many other ethylenically unsaturated monomers or combinations thereof can be emulsion polymerized to form synthetic latexes. Such latexes are commonly employed in paints (latex paints) and coatings. The composition of the present invention may be added to latexes to modify/increase viscosity.

The polymeric thickeners of this invention are advantageous for use with the water-based compositions according to the foregoing description and with compositions containing those materials, especially coating compositions of various types. Mixtures or combinations of two or more thickeners may be used, if desired. Of course the latex polymers used in coating compositions are preferably film-forming at temperatures about 25 degrees C. or less, either inherently or through the use of plasticizers. Such coating compositions include water-based consumer and industrial paints; sizing, adhesives and other coatings for paper, paperboard, textiles; and the like.

Latex paints and coatings may contain various adjuvants, such as pigments, fillers and extenders. Useful pigments include, but are not limited to, titanium dioxide, mica, and iron oxides. Useful fillers and extenders include, but are not limited to, barium sulfate, calcium carbonate, clays, talc, and silica. The compositions of the present invention described herein are compatible with most latex paint systems and provide highly effective and efficient thickening.

The polymer compositions of the present invention may be added to aqueous product systems at a wide range of amounts depending on the desired system properties and end use applications. In latex paints, the composition is added such that the emulsion (HASE) polymer according to the present invention is present at about 0.05 to about 5.0 weight percent and preferably about 0.1 to about 3.0 weight percent based on total weight of the latex paint, including all of its components, such as water, HASE polymer, latex polymer, pigment, and any adjuvants.

The present invention also includes a method of preparing an aqueous coating composition by mixing together at least one latex polymer derived from at least one monomer and blended with at least one pH responsive copolymer as described above, and at least one pigment. Preferably, the latex polymer is in the form of latex polymer dispersion. The additives discussed above can be added in any suitable order to the latex polymer, the pigment, or combinations thereof, to provide these additives in the aqueous coating composition. In the case of paint formulations, the aqueous coating composition preferably has a pH of from 7 to 10.

In formulating latexes and latex paints/coatings, physical properties that may be considered include, but are not limited to, viscosity versus shear rate, ease of application to surface, spreadability, and shear thinning.

V. Emulsion Polymerization to Make Latex Binder for Latex Paint

Emulsion polymerization is discussed in G. Pohlein, "Emulsion Polymerization", Encyclopedia of Polymer Science and Engineering, vol. 6, pp. 1-51 (John Wiley & Sons, Inc., NY, NY, 1986), the disclosure of which is incorporated herein by reference. Emulsion polymerization is a heterogeneous reaction process in which unsaturated monomers or monomer solutions are dispersed in a continuous phase with the aid of an emulsifier system and polymerized with free-radical or redox initiators. The product, a colloidal dispersion of the polymer or polymer solution, is called a latex.

The monomers typically employed in emulsion polymerization to make latex for latex paint include such monomers as methyl acrylate, ethyl acrylate, methyl methacrylate, butyl acrylate, 2-ethyl hexyl acrylate, other acrylates, methacrylates and their blends, acrylic acid, methacrylic acid, styrene, vinyl toluene, vinyl acetate, vinyl esters of higher carboxylic acids than acetic acid, e.g. vinyl versatate, acrylonitrile, acrylamide, butadiene, ethylene, vinyl chloride and the like, and mixtures thereof. This is further discussed below in the section entitled "Latex Monomers".

In the above process, suitable initiators, reducing agents, catalysts and surfactants are well known in the art of emulsion polymerization. Typical initiators include ammonium persulfate (APS), hydrogen peroxide, sodium, potassium or ammonium peroxydisulfate, dibenzoyl peroxide, lauryl peroxide, ditertiary butyl peroxide, 2,2'-azobisisobutyronitrile, t-butyl hydroperoxide, benzoyl peroxide, and the like. Commonly used redox initiation systems are described e.g., by A. S. Sarac in Progress in Polymer Science 24(1999), 1149-1204.

Suitable reducing agents are those which increase the rate of polymerization and include for example, sodium bisulfite, sodium hydrosulfite, sodium formaldehyde sulfoxylate, ascorbic acid, isoascorbic acid, and mixtures thereof.

Suitable catalysts are those compounds which increase the rate of polymerization and which, in combination with the above-described reducing agents, promote decomposition of the polymerization initiator under the reaction conditions. Suitable catalysts include transition metal compounds such as, for example, ferrous sulfate heptahydrate, ferrous chloride, cupric sulfate, cupric chloride, cobalt acetate, cobaltous sulfate, and mixtures thereof.

Emulsion polymerization occurs in the presence of an emulsifier. Typically the mixture contains 0.5 to 6 wt % emulsifier based on weight of latex monomers Typical emulsifiers are ionic or non-ionic surfactants polymerizable or non-polymerizable in the aqueous coating composition including latex polymer. Suitable ionic and nonionic surfactants are alkyl polyglycol ethers such as ethoxylation products of lauryl, tridecyl, oleyl, and stearyl alcohols; alkyl phenol polyglycol ethers such as ethoxylation products of octyl- or nonylphenol, diisopropyl phenol, triisopropyl phenol; alkali metal or ammonium salts of alkyl, aryl or alkylaryl sulfonates, sulfates, phosphates, and the like, including sodium lauryl sulfate, sodium octylphenol glycolether sulfate, sodium dodecylbenzene sulfonate, sodium lauryldiglycol sulfate, and ammonium tritertiarybutyl phenol and penta- and octa-glycol sulfonates, sulfosuccinate salts such as disodium ethoxylated nonylphenol half ester of sulfosuccinic acid, disodium n-octyldecyl sulfosuccinate, sodium dioctyl sulfosuccinate, and the like.

The polymer latex binder can be produced by first preparing an initiator solution comprising the initiator and water. A monomer pre-emulsion is also prepared comprising one or more surfactants (emulsifiers), and other latex monomers to be used to form the latex polymer, water, and additional additives such as NaOH.

Thus, a typical process of emulsion polymerization preferably involves charging water to a reactor and feeding as separate streams a pre-emulsion of the monomer and a solution of the initiator. In particular, the polymer latex binder can be prepared using emulsion polymerization by feeding the monomers used to form the latex binder to a reactor in the presence of at least one initiator and at least one surfactant and polymerizing the monomers to produce the latex binder. Typically the initiator solution and monomer pre-emulsion are continuously added to the reactor over a predetermined period of time (e.g. 1.5-5 hours) to cause polymerization of latex monomers to produce the latex polymer.

Prior to the addition of the initiator solution and the monomer pre-emulsion, a seed latex such as a polystyrene seed latex can be added to the reactor. For example, a small amount of the pre-emulsion and a portion of the initiator may be charged initially at the reaction temperature to produce "seed" latex. The "seed" latex procedure results in better particle-size reproducibility.

Under "normal" initiation conditions, that is initiation conditions under which the initiator is activated by heat, the polymerization is normally carried out at about 60-90° C. A typical "normal" initiated process, for example, could employ ammonium persulfate as initiator at a reaction temperature of 80+/−2° C. Under "redox" initiation conditions, namely initiation conditions under which the initiator is activated by a reducing agent, the polymerization is normally carried out at 60-70° C. Normally, the reducing agent is added as a separate solution. A typical "redox" initiated process, for example, could employ potassium persulfate as the initiator and sodium metabisulfite as the reducing agent at a reaction temperature of 65+/−2° C.

The reactor is operated at desired reaction temperature at least until all the monomers are fed to produce the polymer latex binder. Once the polymer latex binder is prepared, it is preferably chemically stripped thereby decreasing its residual monomer content. Preferably, it is chemically stripped by continuously adding an oxidant such as a peroxide (e.g. t-butylhydroperoxide) and a reducing agent (e.g. sodium acetone bisulfite), or another redox pair such as those described by A. S. Sarac in Progress in Polymer Science 24(1999), 1149-1204, to the latex binder at an elevated temperature and for a predetermined period of time (e.g. 0.5 hours). The pH of the latex binder can then be adjusted and other additives added after the chemical stripping step.

In the above emulsions, the polymer preferably exists as a generally spherical particle, dispersed in water, with a diameter of about 50 nanometers to about 500 nanometers.

For purposes of this description, monomers from which latex polymers may be derived are termed "latex monomers".

The latex monomers fed to a reactor to prepare the polymer latex binder preferably include at least one acrylic monomer selected from the group consisting of acrylic acid, acrylic acid esters, methacrylic acid, and methacrylic acid esters. In addition, the monomers can include styrene, vinyl acetate, or ethylene. The monomers can also include one or more monomers selected from the group consisting of styrene, (alpha)-methyl styrene, vinyl chloride, acrylonitrile, methacrylonitrile, ureido methacrylate, vinyl acetate, vinyl esters of branched tertiary monocarboxylic acids (e.g. vinyl esters commercially available under the mark VEOVA from Shell Chemical Company or sold as EXXAR neo vinyl esters by ExxonMobil Chemical Company), itaconic acid, crotonic acid, maleic acid, fumaric acid, and ethylene. It is also possible to include C4-C8 conjugated dienes such as 1,3-butadiene, isoprene or chloroprene. Commonly used monomers in making acrylic paints are butyl acrylate, methyl methacrylate, ethyl acrylate and the like. Preferably, the monomers include one or more monomers selected from the group consisting of n-butyl acrylate, methyl methacrylate, styrene and 2-ethylhexyl acrylate.

The latex polymer is typically selected from the group consisting of pure acrylics (comprising acrylic acid, methacrylic acid, an acrylate ester, and/or a methacrylate ester as the main monomers); styrene acrylics (comprising styrene and acrylic acid, methacrylic acid, an acrylate ester, and/or a methacrylate ester as the main monomers); vinyl acrylics (comprising vinyl acetate and acrylic acid, methacrylic acid, an acrylate ester, and/or a methacrylate ester as the main monomers); and acrylated ethylene vinyl acetate copolymers (comprising ethylene, vinyl acetate and acrylic acid, methacrylic acid, an acrylate ester, and/or a methacrylate ester as the main monomers). The monomers can also include other main monomers such as acrylamide and acrylonitrile, and one or more functional monomers such as itaconic acid and ureido methacrylate, as would be readily understood by those skilled in the art. In a particularly preferred embodiment, the latex polymer is a pure acrylic such as a butyl acrylate/methyl methacrylate copolymer derived from monomers including butyl acrylate and methyl methacrylate.

In typical acrylic paint compositions the polymer is comprised of one or more esters of acrylic or methacrylic acid, typically a mixture, e.g. about 50/50 by weight, of a high $T_g$ monomer (e.g. methyl methacrylate) and a low $T_g$ monomer (e.g. butyl acrylate), with small proportions, e.g. about 0.5% to about 2% by weight, of acrylic or methacrylic acid. The vinyl-acrylic paints usually include vinyl acetate and butyl acrylate and/or 2-ethyl hexyl acrylate and/or vinyl versatate. In vinyl-acrylic paint compositions, at least 50% of the polymer formed is comprised of vinyl acetate, with the remainder being selected from the esters of acrylic or methacrylic acid. The styrene/acrylic polymers are typically similar to the acrylic polymers, with styrene substituted for all or a portion of the methacrylate monomer thereof.

The latex polymer dispersion preferably includes from about 30 to about 75% solids and a mean latex particle size of from about 70 to about 650 nm. The latex polymer is preferably present in the aqueous coating composition in an amount from about 5 to about 60 percent by weight, and more preferably from about 8 to about 40 percent by weight (i.e. the weight percentage of the dry latex polymer based on the total weight of the coating composition).

The aqueous coating composition is a stable fluid that can be applied to a wide variety of materials such as, for example, paper, wood, concrete, metal, glass, ceramics, plastics, plaster, and roofing substrates such as asphaltic coatings, roofing felts, foamed polyurethane insulation; or to previously painted, primed, undercoated, worn, or weathered substrates. The aqueous coating composition of the invention can be applied to the materials by a variety of techniques well known in the art such as, for example, brush, rollers, mops, air-assisted or airless spray, electrostatic spray, and the like.

V. Liquid Carrier

In one embodiment, the composition of the present invention comprises the selected polymer and a liquid carrier.

In one embodiment, the liquid carrier is an aqueous carrier comprising water and the treatment solution is in the form of a solution, emulsion, or dispersion of the material and additives. In one embodiment, the liquid carrier comprises water and a water miscible organic liquid. Suitable water miscible organic liquids include saturated or unsaturated monohydric alcohols and polyhydric alcohols, such as, for example, methanol, ethanol, isopropanol, cetyl alcohol, benzyl alcohol, oleyl alcohol, 2-butoxyethanol, and ethylene glycol, as well as alkylether diols, such as, for example, ethylene glycol monoethyl ether, propylene glycol monoethyl ether and diethylene glycol monomethyl ether.

As used herein, terms "aqueous medium" and "aqueous media" are used herein to refer to any liquid medium of which water is a major component. Thus, the term includes water per se as well as aqueous solutions and dispersions.

VI. Other Additives

As described above, latex paints and coatings may contain various adjuvants.

The aqueous coating compositions of the invention include less than 2% by weight and preferably less than 1.0% by weight of anti-freeze agents based on the total weight of the aqueous coating composition. For example, the aqueous coating compositions may be substantially free of anti-freeze agents.

The aqueous coating composition typically includes at least one pigment. The term "pigment" as used herein includes non-film-forming solids such as pigments, extenders, and fillers. The at least one pigment is preferably selected from the group consisting of $TiO_2$ (in both anastase and rutile forms), clay (aluminum silicate), $CaCO_3$ (in both ground and precipitated forms), aluminum oxide, silicon dioxide, magnesium oxide, talc (magnesium silicate), barytes (barium sulfate), zinc oxide, zinc sulfite, sodium oxide, potassium oxide and mixtures thereof. Suitable mixtures include blends of metal oxides such as those sold under the marks MINEX (oxides of silicon, aluminum, sodium and potassium commercially available from Unimin Specialty Minerals), CELITES (aluminum oxide and silicon dioxide commercially available from Celite Company), ATOMITES (commercially available from English China Clay International), and ATTAGELS (commercially available from Engelhard). More preferably, the at least one pigment includes TiO2, CaCO3 or clay. Generally, the mean particle sizes of the pigments range from about 0.01 to about 50 microns. For example, the TiO2 particles used in the aqueous coating composition typically have a mean particle size of from about 0.15 to about 0.40 microns. The pigment can be added to the aqueous coating composition as a powder or in slurry form. The pigment is preferably present in the aqueous coating composition in an amount from about 5 to about 50 percent by weight, more preferably from about 10 to about 40 percent by weight.

The coating composition can optionally contain additives such as one or more film-forming aids or coalescing agents. Suitable firm-forming aids or coalescing agents include plasticizers and drying retarders such as high boiling point polar solvents. Other conventional coating additives such as, for example, dispersants, additional surfactants (i.e. wetting agents), rheology modifiers, defoamers, thickeners, additional biocides, additional mildewcides, colorants such as colored pigments and dyes, waxes, perfumes, co-solvents, and the like, can also be used in accordance with the invention. For example, non-ionic and/or ionic (e.g. anionic or cationic) surfactants can be used to produce the polymer latex. These additives are typically present in the aqueous coating composition in an amount from 0 to about 15% by weight, more preferably from about 1 to about 10% by weight based on the total weight of the coating composition.

The aqueous coating composition typically includes less than 10.0% of anti-freeze agents based on the total weight of the aqueous coating composition. Exemplary anti-freeze agents include ethylene glycol, diethylene glycol, propylene glycol, glycerol (1,2,3-trihydroxypropane), ethanol, methanol, 1-methoxy-2-propanol, 2-amino-2-methyl-1-propanol, and FTS-365 (a freeze-thaw stabilizer from Inovachem Specialty Chemicals). More preferably, the aqueous coating composition includes less than 5.0% or is substantially free (e.g. includes less than 0.1%) of anti-freeze agents. Accordingly, the aqueous coating composition of the invention preferably has a VOC level of less than about 100 g/L and more preferably less than or equal to about 50 g/L.

The balance of the aqueous coating composition of the invention is water. Although much of the water is present in the polymer latex dispersion and in other components of the aqueous coating composition, water is generally also added separately to the aqueous coating composition. Typically, the aqueous coating composition includes from about 10% to about 85% by weight and more preferably from about 35% to about 80% by weight water. Stated differently, the total solids content of the aqueous coating composition is typically from about 15% to about 90%, more preferably, from about 20% to about 65%.

The coating compositions are typically formulated such that the dried coatings comprise at least 10% by volume of dry polymer solids, and additionally 5 to 90% by volume of non-polymeric solids in the form of pigments. The dried coatings can also include additives such as plasticizers, dispersants, surfactants, rheology modifiers, defoamers, thickeners, additional biocides, additional mildewcides, colorants, waxes, and the like, that do not evaporate upon drying of the coating composition.

VIII. Personal Care

The pH responsive polymer of the present invention is suitable in the preparation of personal care (cosmetics, toiletries, health and beauty aids, cosmeceuticals) and topical health care products, including without limitation, hair care products, such as shampoos (including combination shampoos, such as "two-in-one" conditioning shampoos); post-shampoo rinses; setting and style maintenance agents including setting aids, such as gels and sprays, grooming aids, such as pomades, conditioners, perms, relaxers, hair smoothing products, and the like; skin care products (facial, body, hands, scalp and feet), such as creams, lotions, conditioners, and cleansing products; anti-acne products; anti-aging products (exfoliant, keratolytic, anticellulite, anti-wrinkle, and the like); skin protectants such as sunscreens, sunblock, barrier creams, oils, silicones, and the like; skin color products (whiteners, lighteners, sunless tanning accelerators, and the like); hair colorants (hair dyes, hair color rinses, highlighters, bleaches and the like); pigmented skin colorants (face and body makeups, foundation creams, mascara, rouge, lip products, and the like); bath and shower products (body cleansers, body wash, shower gel, liquid soap, soap bars, syndet bars, conditioning liquid bath oil, bubble bath, bath powders, and the like); nail care products (polishes, polish removers, strengtheners, lengtheners, hardeners, cuticle removers, softeners, and the like); and any aqueous acidic to basic composition to which an effective amount of the hydrophobic polymer can be incorporated for achieving a beneficial or desirable, physical or chemical, effect therein during storage and/or usage.

In one embodiment, the present invention is directed to a personal care composition comprising water, one or more surfactants, and a pH responsive polymer according to the present invention.

In one embodiment, the personal care composition comprises, based on 100 parts by weight ("pbw") of the personal care composition, from about 10 to about 80 pbw, more typically from about 20 to about 70 pbw, water, from about 1 to about 50 pbw of one or more surfactants and from about 0.05 to about 20 pbw of the pH responsive polymer of the present invention.

Suitable surfactants include anionic surfactants, cationic surfactants, non-ionic surfactants, zwitterionic surfactants, and mixtures thereof.

Suitable anionic surfactants are known compounds and include, for example, linear alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, dialkyl phosphates, sarcosinates, isethionates, and taurates, as well as mixtures thereof, such as for example, ammonium lauryl sulfate, ammonium laureth sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium trideceth sulfate, sodium tridecyl sulfate, ammonium trideceth sulfate, ammonium tridecyl sulfate, sodium cocoyl isethionate, disodium laureth sulfosuccinate, sodium methyl oleoyl taurate, sodium laureth carboxylate, sodium trideceth carboxylate, sodium monoalkyl phosphate, sodium dialkyl phosphate, sodium lauryl sarcosinate, lauroyl sarcosine, cocoyl sarcosinate, ammonium cocyl sulfate, sodium cocyl sulfate, potassium cocyl sulfate, monoethanolamine cocyl sulfate, sodium tridecyl benzene sulfonate, sodium dodecyl benzene sulfonate, and mixtures thereof.

The cationic counterion of the anionic surfactant is typically a sodium cation but may alternatively be a potassium, lithium, calcium, magnesium, ammonium cation, or an alkyl ammonium anion having up to 6 aliphatic carbon atoms, such as anisopropylammonium, monoethanolammonium, diethanolammonium, or triethanolammonium cation. Ammonium and ethanolammonium salts are generally more soluble than the sodium salts.

Mixtures of the above cations may be used.

Suitable cationic surfactants are known compounds and include, for example, mono-cationic surfactants according to structure (XX) below:

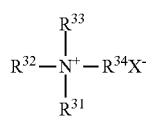

XX wherein:

R31, R32, R33 and R34 are independently hydrogen or an organic group, provided that at least one of R31, R32, R33 and R34 is not hydrogen, and X⁻ is an anion, as well as mixtures of such compounds If one to three of the R31, R32, R33 and R34 groups are each hydrogen, then the compound may be referred to as an amine salt. Some examples of cationic amine salts include polyethoxylated (2) oleyl/stearyl amine, ethoxylated tallow amine, cocoalkylamine, oleylamine, and tallow alkyl amine.

For quaternary ammonium compounds (generally referred to as quats) R31, R32, R33 and R34 may be the same or different organic group, but may not be hydrogen. In one embodiment, R31, R32, R33 and R34 are each C8-C24 branched or linear hydrocarbon groups which may comprise additional functionality such as, for example, fatty acids or derivatives thereof, including esters of fatty acids and fatty acids with alkoxylated groups; alkyl amido groups; aromatic rings; heterocyclic rings; phosphate groups; epoxy groups; and hydroxyl groups. The nitrogen atom may also be part of a heterocyclic or aromatic ring system, e.g., cetethyl morpholinium ethosulfate or steapyrium chloride.

Examples of quaternary ammonium compounds of the monoalkyl amine derivative type include: cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl dimethyl (2) hydroxyethyl ammonium dihydrogen phosphate (also known as hydroxyethyl cetyldimonium phosphate), babassuamidopropalkonium chloride, cocotrimonium chloride, distearyldimonium chloride, wheat germ-amidopropalkonium chloride, stearyl octyldimonium methosulfate, isostearaminopropalkonium chloride, dihydroxypropyl PEG-5 linoleaminium chloride, PEG-2 stearmonium chloride, Quaternium 18, Quaternium 80, Quaternium 82, Quaternium 84, behentrimonium chloride, dicetyl dimonium chloride, behentrimonium methosulfate, tallow trimonium chloride and behenamidopropyl ethyl dimonium ethosulfate.

Quaternary ammonium compounds of the dialkyl amine derivative type include, for example, distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bisstearyldimonium chloride, and mixtures thereof.

Quaternary ammonium compounds of the imidazoline derivative type include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Typical cationic surfactants comprise dialkyl derivatives such as dicetyl dimonium chloride and distearyldimonium chloride; branched and/or unsaturated cationic surfactants such as isostearylaminopropalkonium chloride or olealkonium chloride; long chain cationic surfactants such as stearalkonium chloride and behentrimonium chloride; as well as mixtures thereof.

Suitable anionic counterions for the cationic surfactant include, for example, chloride, bromide, methosulfate, ethosulfate, lactate, saccharinate, acetate and phosphate anions.

Suitable nonionic surfactants are known compounds and include amine oxides, fatty alcohols, alkoxylated alcohols, fatty acids, fatty acid esters, and alkanolamides. Suitable amine oxides comprise, (C10-C24) saturated or unsaturated branched or straight chain alkyl dimethyl oxides or alkyl amidopropyl amine oxides, such as for example, lauramine oxide, cocamine oxide, stearamine oxide, stearamidopropylamine oxide, palmitamidopropylamine oxide, decylamine oxide as well as mixtures thereof. Suitable fatty alcohols include, for example, (C10-C24) saturated or unsaturated branched or straight chain alcohols, more typically (C10-C20) saturated or unsaturated branched or straight chain alcohols, such as for example, decyl alcohol, lauryl alcohol, myristyl alcohol, cetyl alcohol, stearyl alcohol, oleyl alcohol, linoleyl alcohol and linolenyl alcohol, and mixtures thereof. Suitable alkoxylated alcohols include alkoxylated, typically ethoxylated, derivatives of (C10-C24) saturated or unsaturated branched or straight chain alcohols, more typically (C10-C20) saturated or unsaturated branched or straight chain alcohols, which may include, on average, from 1 to 22 alkoxyl units per molecule of alkoxylated alcohol, such as, for example, ethoxylated lauryl alcohol having an average of 5 ethylene oxide units per molecule. Mixtures of these alkoxylated alcohols may be used. Suitable fatty acids include (C10-C24) saturated or unsaturated carboxylic acids, more typically (C10-C22) saturated or unsaturated carboxylic acids, such as, for example, lauric acid, oleic acid, stearic acid, myristic acid, cetearic acid, isostearic acid, linoleic acid, linolenic acid, ricinoleic acid, elaidic acid, arichidonic acid, myristoleic acid, and palmitoleic acid, as well as neutralized versions thereof. Suitable fatty acid esters include esters of (C10-C24) saturated or unsaturated carboxylic acids, more typically (C10-C22) saturated or unsaturated carboxylic acids, for example, propylene glycol isostearate, propylene glycol oleate, glyceryl isostearate, and glyceryl oleate, and mixtures thereof. Suitable alkanolamides include aliphatic acid alkanolamides, such as cocamide MEA (coco monoethanolamide) and cocamide MIPA (coco monoisopropanolamide), as well as alkoxylated alkanolamides, and mixtures thereof.

Suitable amphoteric surfactants are known compounds and include for example, derivatives of aliphatic secondary and tertiary amines in which the aliphatic radical can be straight chain or branched and wherein one of the aliphatic substituents contains from about 8 to about 18 carbon atoms and one contains an anionic water-solubilizing group as well as mixtures thereof. Specific examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates, and alkyl amphopropionates, as well as alkyl iminopropionates, alkyl iminodipropionates, and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

In one embodiment, the amphoteric surfactant comprises sodium lauroampoacetate, sodium lauroampopropionate, disodium lauroampodiacetate, sodium cocoamphoacetate, disodium cocoamphodiacetate or a mixture thereof.

Suitable Zwitterionic surfactants are known compounds. Any Zwitterionic surfactant that is acceptable for use in the intended end use application and is chemically stable at the required formulation pH is suitable as the optional Zwitterionic surfactant component of the composition of the present invention, including, for example, those which can be broadly described as derivatives of aliphatic quaternary ammonium, phosphonium, and sulfonium compounds in which the aliphatic radicals can be straight chain or branched and wherein one of the aliphatic substituents contains from about 8 to about 24 carbon atoms and one contains an anionic water-solubilizing group such as carboxyl, sulfonate, sulfate, phosphate or phosphonate. Specific examples of suitable Zwitterionic surfactants include alkyl betaines, such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine and alkylamidopropylhydroxy sultaines.

In one embodiment, the personal care composition further comprises an electrolyte, typically in an amount of up to about 20 pbw per 100 pbw of the personal care composition. Suitable electrolytes are known compounds and include salts of multivalent anions, such as potassium pyrophosphate, potassium tripolyphosphate, and sodium or potassium citrate, salts of multivalent cations, including alkaline earth metal salts such as calcium chloride and calcium bromide, as well as zinc halides, barium chloride and calcium nitrate, salts of monovalent cations with monovalent anions, including alkali metal or ammonium halides, such as potassium chloride, sodium chloride, potassium iodide, sodium bromide, and ammonium bromide, alkali metal or ammonium nitrates, and polyelectrolytes, such as uncapped polyacrylates, polymaleates, or polycarboxylates, lignin sulfonates or naphthalene sulfonate formaldehyde copolymers.

In one embodiment, the personal care composition comprises water, an anionic surfactant, a structuring agent for the anionic surfactant, and a pH responsive polymer according to the present invention and exhibits one or more lamellar surfactant phases. "Lamellar surfactant phases" are phases which comprise one or more surfactant bilayers, typically a plurality of surfactant bilayers separated by liquid medium. Lamellar phases include spherulite phases and the typical form of the liquid crystal G-phase, as well as mixtures thereof. "G-phases", which are sometimes referred to in the literature as "L, phases", are typically pourable, non-Newtonian, anisotropic products that are cloudy looking and exhibit a characteristic "smeary" appearance on flowing. Lamellar phases can exist in several different forms, including domains of parallel sheets, which constitute the bulk of the typical G-phases described above and spherulites formed from a number of concentric spherical shells, each of which is a bilayer of surfactant. In this specification the term "G-phase" will be reserved for compositions, which are at least partly of the former type. The spherulites are typically between 0.1 and 50 microns in diameter and so differ fundamentally from micelles. The surfactant phase morphology of the structured surfactant composition is observed, for example, using an optical microscope under cross-polarized light at about 40× magnification.

In one embodiment, the personal care composition of the present invention exhibits structured surfactant properties, that is, shear-thinning viscosity and a capacity to suspend water insoluble or partially water soluble components.

As used herein in reference to viscosity, the terminology "shear-thinning" means that such viscosity decreases with an increase in shear rate. Shear-thinning may be characterized as a "non-Newtonian" behavior, in that it differs from that of a classical Newtonian fluid, for example, water, in which viscosity is not dependent on shear rate.

As used herein in reference to a component of an aqueous composition, the terminology "water insoluble or partially water soluble components" means that the component is present in the aqueous composition at a concentration above the solubility limit of the component so that, in the case of a water insoluble component, the component remains substantially non-dissolved in the aqueous composition and, in the case of a partially water soluble component, at least a portion of such component remains undissolved in the aqueous composition.

As used herein, characterization of an aqueous composition as "capable of suspending", or as being "able of suspend" water insoluble or partially water insoluble components means that the composition substantially resists flotation of such components in the composition or sinking of such components in such composition so that such components appear to be neutrally buoyant in such composition and remain at least substantially suspended in such composition under the anticipated processing, storage, and use conditions for such aqueous composition.

In one embodiment, the personal care composition of the present invention comprises, based on 100 pbw of the composition from about 5 to about 40 parts pbw, more typically from about 10 to about 30 pbw, and still more typically from about 15 to about 25 pbw, of the anionic surfactant and from about 0.1 to about 25 pbw, more typically, from about 0.5 to about 10 pbw, of a structuring agent.

In one embodiment, the pH of the lamellar phase containing personal care composition is from about 5.0 to about 7.0, more typically from about 5.5 to about 6.5.

Suitable anionic surfactants include those described above. In one embodiment of the lamellar phase containing personal care composition, the anionic surfactant comprises one or more branched and/or unsaturated anionic surfactants. Suitable branched anionic surfactants include, for example, sodium trideceth sulfate, sodium tridecyl sulfate, ammonium trideceth sulfate, and ammonium tridecyl sulfate.

Suitable structuring agents include cationic surfactants, amphoteric surfactants, fatty alcohols, alkoxylated alcohols, fatty acids, fatty acid esters, alkanolamides, amine oxides, and electrolytes, and mixtures thereof. An effective amount of such structuring agent is one that promotes and/or does not interfere with the formation of a lamellar surfactant phase. Suitable cationic surfactants, amphoteric surfactants, fatty alcohols, alkoxylated alcohols, fatty acids, fatty acid esters, alkanolamides, amine oxides, and electrolytes are described above.

Typically, the greater the amount of surfactant present in relation to its solubility, the smaller the amount electrolyte that may be required in order to form a structure capable of supporting solid materials and/or to cause flocculation of the structured surfactant. In one embodiment, the composition contains a sufficient amount of an electrolyte to promote formation lamellar surfactant phases.

In one embodiment, the personal care composition of the present invention further comprises, typically in an amount of from greater than 0 pbw to about 50 pbw, more typically form about 1 to about 30 pbw, per 100 pbw of the personal care composition, one or more "benefit agents" that is, materials that provide a personal care benefit, such as moisturizing or conditioning, to the user of the personal care composition, such as, for example, emollients, moisturizers, conditioners, polymers, vitamins, abrasives, UV absorbers, antimicrobial agents, anti-dandruff agents, fragrances, and/or appearance modifying additives, such as, for example, colored particles or reflective particles, which may be in the form of a solid, liquid, or gas and may be insoluble or are only partly soluble in the personal care composition. Mixtures of the benefit agents may be used.

In one embodiment, the personal care composition is a hair styling composition. Suitable hair styling compositions may be in the form of a gel, mousse, or spray and may be applied to the hair and/or skin, for example, by hand or by spraying, as appropriate in view of the form of the composition.

In one embodiment, the personal care composition is a hair styling gel that comprises a hair styling polymer, a pH responsive polymer of the present invention, and a carrier, such as water, a (C2-C6)alkanol, or a mixture thereof.

Suitable hair styling polymers typically comprise multiple cationic sites per molecule and include, for example, polyquaternium-11, polyquaternium4, polyquaternium-7, polyquaternium-16, polyquaternium-28, polyquaternium-44, polyquaternium-46, polyquaternium-55, polyquaternium-68 and polyquaternium-88. Suitable hair styling polymers also include, but are not limited to copolymers of polyvinylpyrrolidone, vinyl acetate, polyvinylcaprolactam, methylether maleic acid, acrylamides, octylacrylamide, butylaminoethyl, crotonic acid, dimethylaminopropyl methacrylate and dimethylaminoethyl methacrylate, and mixtures thereof.

As used herein, the term "mousse" means a composition that is in the form of a foam when applied. In one embodiment, the personal care composition is a hair styling mousse is packaged in a pressurized container and comprises a hair styling polymer, a pH responsive polymer of the present invention, a carrier, such as water, a (C2-C6)alkanol, a propellant suitable for foaming the composition when the composition is dispensed from the container. Suitable propellants are liquefiable gases, such as, for example, propane, butane, isobutane, nitrogen, carbon dioxide, nitrous oxide, 1,2-difluoroethane.

In one embodiment, the personal care composition is a hair spray composition suitable for spray application from a container that is equipped with a mechanical sprayer, comprising a hair styling polymer, a pH responsive polymer of the present invention, and a carrier, such as water, a (C2-C6)alkanol, or a mixture thereof.

In one embodiment, the personal care composition is an aerosol hair spray composition suitable for spray application from a pressurized container and comprises, a hair styling polymer, a carrier, typically a (C1-C6)alkanol or a (C7-C10) isoparaffin, a pH responsive polymer of the present invention, and a propellant suitable for aerosol delivery of the hair spray composition to the hair. Suitable propellants are those described above in regard to the hair styling mousse embodiment of the personal care composition of the present invention.

The hair styling gel, mousse, and hair spray may in each case, optionally further comprise one or more emollients, conditioning agents, shine enhancers, moisture and heat sensitive moieties, or a mixture thereof. Suitable emollients include, for example, PEG-40 castor oil, glycerol, propylene glycol, butylene glycol. Suitable conditioning and shine agents include, for example, quaternized and/or hydrolyzed proteins of honey, soy, wheat, guar or maize, cetyl alcohol, stearyl alcohol, ceteareth-20, isopropyl palmitate, cyclopentasiloxane, cyclomethicone, trimethylsilyamodimethicone, phenyltrimethicone, ethoxylated/propylated dimethicone, dimethiconol, panthenol, tocopherol acetate, tocopherol, cetrimmonium chloride, hair keratin and silk amino acids and ethoxylated/propoxylated waxes of fruit and vegetable origin.

The personal care composition according to the present invention may optionally further comprise one or more adjuvants, such as, for example, preservatives such as benzyl alcohol, methyl paraben, propyl paraben and imidazolidinyl urea; pH adjusting agents such as citric acid, succinic acid, phosphoric acid, sodium hydroxide, sodium carbonate; dyes, and sequestering agents such as disodium ethylenediamine tetra-acetate.

In general, personal care compositions may optionally comprise, based on 100 pbw of the personal care composition and independently for each such adjuvant, from about 0 to about 10 pbw, typically from 0.5 pbw to about 5.0 pbw, of such optional adjuvants, depending on the desired properties of the personal care composition.

The pH responsive polymer of the present application is useful as a component in aqueous fluid compositions used in oilfield applications.

In one embodiment, an aqueous fluid composition of the present invention comprises water and a pH responsive polymer of the present invention, typically from about 0.05 to about 40 pbw, more typically 0.1 pbw to 20 pbw, even more typically form about 1 to about 10 pbw of the pH responsive polymer per 100 pbw composition, wherein the pH of the composition is greater than or equal to about 6, more typically, from about 6 to about 10.

IX. Use with Materials in Geological Formations
Fracturing Fluids

In one embodiment, the aqueous fluid composition of the present invention is used as the fracturing fluid in a method for hydraulic fracturing of a geologic formation to stimulate the production of fluids, such as oil and/or natural gas, from the formation. The fracturing fluid is injected through a wellbore and against a surface of the formation at a pressure and flow rate at least sufficient to initiate and/or extend one or more fractures in the formation. Typically, the fracturing fluid further comprises a proppant dispersed in the fracturing fluid. Suitable proppants are inorganic particles, such as sand, bauxite particles, or glass beads and are typically in the range of from about 20 to about 40 mesh. Such fracturing fluid compositions typically contain, based on 100 pbw of the liquid component of such composition, from about 90 pbw to about 100 pbw water, from about 0.1 pbw to about 10 pbw pH responsive polymer, and from about 10 pbw to about 150 pbw proppant. The proppant particles are transported into fractures in the geologic formation by the pressurized fracturing fluid stream and keep the fractures from closing back down when the stream of fracturing fluid is discontinued. The proppant-filled fractures provide permeable channels through which the formation fluids can flow to the wellbore and then be withdrawn. Hydraulic fracturing fluids are subject to high temperatures and shear rates.

The polymer and composition of the present invention may be used in the fracturing fluid in an amount of from 0.01 to 5% by weight of the fluid.

Crosslinking Agent

A crosslinking agent may be used with the fracturing fluids. The crosslinking agents used may include aluminum or antimony or Group 4 transition metal compound crosslinking agents. The crosslinking agent may include zirconium, titanium and hafnium crosslinking agents, and combinations of these, and may include organo-metallic compounds. Examples of suitable zirconium crosslinking agents include zirconium triethanolamine, L-glutamic acid-triethanolamine-zirconium, zirconium diethanolamine, zirconium tripropanolamine, and zirconium lactate complexes, and/or the related salts, and/or their mixtures. Examples of titanium crosslinking agents include titanium triethanolamine, dihydroxybis(ammonium lactato)titanium, and titanium acetylacetonate. The crosslinking agent may be included in the fluid in an amount of from about 0.01% to about 1.5% by weight of the fluid, more particularly, from about 0.02% to about 0.3% by weight of the fluid.

Buffering Agent

A hydroxyl ion releasing agent or buffering agent may be employed to adjust the pH or buffer the fluid, i.e., moderate amounts of either a strong base or acid may be added without causing any large change in pH value of the fluid. These may useful in changing the rate of crosslinking. Alkaline amine or polyamine compounds useful to raise the pH to the desirable level are outlined in U.S. Pat. No. 4,579,670, and include tetramethylenediamine, triethylenetetramine, tetraethylenepentamine (TEPA), diethylenetriamine, triethylenediamine, triethylenepentamine, ethylenediamen and similar compounds. The alkali metal hydroxides, e.g., sodium hydroxide, and carbonates can also be used. Other acceptable materials are $Ca(OH)_2$, $Mg(OH)_2$, $Bi(OH)_3$, $Co(OH)_2$, $Pb(OH)_2$, $Ni(OH)_2$, $Ba(OH)_2$, and $Sr(OH)_2$. Acids such as hydrochloric acid, sulfuric acid, nitric acid, citric acid, acetic acid, fumaric acid, maleic acid, can be used to lower the pH.

In various embodiments, the buffering agent is a combination of a weak acid and a salt of the weak acid; an acid salt with a normal salt; or two acid salts. Examples of suitable buffering agents are acetic acid-Na acetate; $NaH_2PO_4$—$Na_2PO_4$; sodium carbonate-sodium bicarbonate; and sodium bicarbonate, or other like agents. By employing a buffering agent instead of merely a hydroxyl ion producing material, a fluid is provided which is more stable to a wide range of pH values found in local water supplies and to the influence of acidic materials located in formations and the like.

The fracturing fluids may contain a gas component, as discussed above. The gas component may be provided from any suitable gas that forms an energized fluid or foam when introduced into the aqueous medium. See, for example, U.S. Pat. No. 3,937,283 (Blauer et al.), hereinafter incorporated by reference. The gas component may comprise a gas selected from nitrogen, air, argon, carbon dioxide, and any mixtures thereof. Particularly useful are the gas components of nitrogen or carbon dioxide, in any quality readily available. The gas component may assist in the fracturing, and also the capacity of the fluid to carry solids, such as proppants. The presence of the gas also enhances the flow-back of the fluid to facilitate cleanup. The fluid may contain from about 10% to about 90% volume gas component based upon total fluid volume percent, more particularly from about 20% to about 80% volume gas component based upon total fluid volume percent, and more particularly from about 30% to about 70% volume gas component based upon total fluid volume percent.

Fracturing fluids based on the invention may also comprise a breaker. The purpose of this component is to "break" or diminish the viscosity of the fluid so that this fluid is more easily recovered from the formation during cleanup. With regard to breaking down viscosity, oxidizers, enzymes, or acids may be used. Breakers reduce the polymer's molecular weight by the action of an acid, an oxidizer, an enzyme, or some combination of these on the polymer itself. The breakers may include persulfates such as ammonium persulfate, sodium persulfate, and potassium persulfate, bromates such as sodium bromate and potassium bromate, periodates, metal peroxides such as calcium peroxide, chlorites, and the like, and the combinations of these breakers, live or encapsulated.

Embodiments of the invention used as fracturing fluids may also include proppant particles substantially insoluble in the fluids of the formation. Proppant particles carried by the treatment fluid remain in the fracture created, thus propping open the fracture when the fracturing pressure is released and the well is put into production. Suitable proppant materials include, but are not limited to, sand, walnut shells, sintered bauxite, glass beads, ceramic materials, naturally occurring materials, or similar materials. Mixtures of proppants can be used as well. If sand is used, it will typically be from about 20 mesh (0.841 mm) to about 100 mesh (0.0059 mm) in size. With synthetic proppants, mesh sizes of about 8 (0.937 mm) or greater may be used. Naturally occurring materials may be underived and/or unprocessed naturally occurring materials, as well as materials based on naturally occurring materials that have been processed and/or derived. Suitable examples of naturally occurring particulate materials for use as proppants include, but are not necessarily limited to: ground or crushed shells of nuts such as walnut, coconut, pecan, almond, ivory nut, brazil nut, etc.; ground or crushed seed shells (including fruit pits) of seeds of fruits such as plum, olive, peach, cherry, apricot, etc.; ground or crushed seed shells of other plants such as maize (e.g., corn cobs or corn kernels), etc.; processed wood materials such as those derived from woods such as oak, hickory, walnut, poplar, mahogany, etc. including such woods that have been processed by grinding, chipping, or other form of particalization, processing, etc. Further information on nuts and composition thereof may be found in Encyclopedia of Chemical Technology, Edited by Raymond E. Kirk and Donald F. Othmer, Third Edition, John Wiley & Sons, Volume 16, pages 248-273 (entitled "Nuts"), Copyright 1981, which is incorporated herein by reference.

The concentration of proppant in the fluid can be any concentration known in the art, and will preferably be in the range of from about 0.03 to about 3 kilograms of proppant added per liter of liquid phase. Also, any of the proppant particles can further be coated with a resin to potentially improve the strength, clustering ability, and flow back properties of the proppant.

Aqueous Media

The aqueous medium of the fracturing fluids of the present invention may be water or brine. In those embodiments of the invention where the aqueous medium is a brine, the brine is water comprising an inorganic salt or organic salt. Inorganic salts may include alkali metal halides, such as potassium chloride. The carrier brine phase may also comprise an organic salt, such as sodium or potassium formate. Inorganic divalent salts include calcium halides, such as calcium chloride or calcium bromide. Sodium bromide, potassium bromide, or cesium bromide may also be used. The salt may be chosen for compatibility reasons i.e. where the reservoir drilling fluid used a particular brine phase and the completion/clean up fluid brine phase is chosen to have the same brine phase. Typical salt levels are 2 to 30 wt % salt based on overall composition of the aqueous brine. The most common level of salt in brine is 2-10 weight % sodium chloride, potassium chloride or mixtures thereof based on overall composition of the aqueous brine.

Fiber Component

A fiber component may be included in the fracturing fluids of the invention to achieve a variety of properties including improving particle suspension, and particle transport capabilities, and gas phase stability. Fibers used may be hydrophilic or hydrophobic in nature, but hydrophilic fibers may be useful for some applications. Fibers can be any fibrous material, such as, but not necessarily limited to, natural organic fibers, comminuted plant materials, synthetic polymer fibers (by non-limiting example polyester, polyaramide, polyamide, novoloid or a novoloid-type polymer), fibrillated synthetic organic fibers, ceramic fibers, inorganic fibers, metal fibers, metal filaments, carbon fibers, glass fibers, ceramic fibers, natural polymer fibers, and any mixtures thereof. Particularly useful fibers are polyester fibers coated to be highly hydrophilic, such as, but not limited to, DACRON polyethylene terephthalate (PET) fibers available from Invista Corp. Wichita, Kans., USA, 67220. Other examples of useful fibers include, but are not limited to, polylactic acid polyester fibers, polyglycolic acid polyester fibers, polyvinyl alcohol fibers, and the like. When used in fluids of the invention, the fiber component may be include at concentrations from about 1 to about 15 grams per liter of the liquid phase of the fluid, in certain applications the concentration of fibers may be from about 2 to about 12 grams per liter of liquid, and in others from about 2 to about 10 grams per liter of liquid.

Other Optional Ingredients

Fluid embodiments of fracturing fluids of the invention may further contain other additives and chemicals known to be commonly used in oilfield applications by those skilled in the art. These include, but are not necessarily limited to, materials such as surfactants in addition to those mentioned herein, clay stabilizers such as tetramethyl ammonium chloride and/or potassium chloride, breaker aids in addition to those mentioned herein, oxygen scavengers, alcohols, scale inhibitors, corrosion inhibitors, fluid-loss additives, bactericides, and the like. Also, they may include a co-surfactant to optimize viscosity or to minimize the formation of stable emulsions that contain components of crude oil or a polysaccharide or chemically modified polysaccharide, polymers such as cellulose, derivatized cellulose, guar gum, derivatized guar gum, xanthan gum, or synthetic polymers such as polyacrylamides and polyacrylamide copolymers, oxidizers such as ammonium persulfate and sodium bromate, and biocides such as 2,2-dibromo-3-nitrilopropionamine. The fluid should be substantially devoid of hectorite clay or other clay components and such components may be present in the fluid only in amounts of less than 0.1% by weight.

Aqueous fluid embodiments of the invention may also comprise an organoamino compound. Examples of suitable organoamino compounds include, but are not necessarily limited to, tetraethylenepentamine (TEPA), triethylenetetramine, pentaethylenehexamine, triethanolamine, and the like, or any mixtures thereof. When organoamino compounds are used in fluids of the invention, they are incorporated at an amount from about 0.01 wt % to about 2.0 wt % based on total liquid phase weight. The organoamino compound may be incorporated in an amount from about 0.05 wt % to about 1.0 wt % based on total weight of the fluid. A particularly useful organoamino compound is tetraethylenepentamine (TEPA).

Hydraulic Fracturing Techniques

The fluids of the invention may be used for hydraulically fracturing a subterranean formation. Techniques for hydraulically fracturing a subterranean formation are known to persons of ordinary skill in the art, and involve pumping the fracturing fluid into the borehole and out into the surrounding formation. The fluid pressure is above the minimum in situ rock stress, thus creating or extending fractures in the formation. See Stimulation Engineering Handbook, John W. Ely, Pennwell Publishing Co., Tulsa, Okla. (1994), U.S. Pat. No. 5,551,516 (Normal et al.), "Oilfield Applications", Encyclopedia of Polymer Science and Engineering, vol. 10, pp. 328-366 (John Wiley & Sons, Inc. New York, N.Y., 1987) and references cited therein, the disclosures of which are incorporated herein by reference thereto.

In the fracturing treatment, fluids of the present invention may be used in the pad treatment, the proppant stages, or both. The components of the liquid phase may be mixed on the surface. Alternatively, the fluid may be prepared on the surface and pumped down tubing while any gas component could be pumped down the annulus to mix down hole, or vice versa.

In hydraulic fracturing the fracturing fluid comprising water soluble polymer and at least one nonionic surfactant is pumped into the targeted formation at a rate in excess of what can be dissipated through the natural permeability of the formation rock. The fracturing fluids result in a pressure build up until such pressure exceeds the strength of the formation rock. When this occurs, the formation rock fails and a so-called "fracture" is initiated. With continued pumping, the fracture grows in length, width and height.

At a predetermined time in the pumping process, solid particulate is typically added to the fluid that is being pumped. This particulate is carried down the well, out of the wellbore and deposited in the created fracture. It is the purpose of this specially designed particulate to keep the fracture from "healing" to its initial position (after pumping has ceased). The particulate is said to be propping open the fracture and is therefore designated as "proppant". The fracture, which is generated by the application of this stimulation technique, creates a conductive path to the wellbore for the hydrocarbon.

Typical proppant is selected from the group consisting of gravel, quartz sand grains, sintered bauxite, glass and ceramic beads, walnut shell fragments, or aluminum pellets. The fracturing fluid may also include a thermal stabilizer, for example sodium thiosulfate, methanol, ethylene glycol, isopropanol, thiourea, and/or sodium thiosulfite. The fracturing fluid may also include KCl as a clay stabilizer.

X. Home Care or Industrial Care Compositions

In one embodiment, the present invention is directed to a home care or industrial cleaning composition, such as a liquid detergent, a laundry detergent, a hard surface cleanser, a dish wash liquid, or a toilet bowl cleaner, comprising water, one or more surfactants, and a polymer of the present invention. Suitable surfactants include those described above in regard to the personal care composition embodiments of the present invention. Such cleaning compositions may optionally further comprise one or more of water miscible organic solvents, such as alcohols and glycols, and/or one or more additives.

Suitable additives are known in the art and include, for example, organic builders, such as organophosphonates, inorganic builders, such as ammonium polyphosphates, alkali metal pyrophosphates, zeolites, silicates, alkali metal borates, and alkali metal carbonates, bleaching agents, such as perborates, percarbonates, and hypochlorates, sequestering agents and anti-scale agents, such as citric acid and ethylenediaminetetraacetic acid, inorganic acids, such as phosphoric acid and hydrochloric acid, organic acids, such as acetic acid, abrasives, such as silica or calcium carbonate, antibacterial agents or disinfectants, such as triclosan and cationic biocides, for example (N-alkyl)benzyldimethylammonium chlorides, fungicides, enzymes, opacifing agents, pH modifiers, dyes, fragrances, and preservatives.

In an embodiment the home care or industrial cleaner benefit agent is selected from the group consisting of soil release agents, fabric softener, surfactants, builders, binders, bleach and fragrances.

In an embodiment the home care or industrial cleaning composition for cleaning fabrics or hard surfaces comprising, the composition of the present invention and a surfactant and a home care or industrial cleaner benefit agent.

In an embodiment the composition is a detergent composition and comprises: the polymer, at least one detersive surfactant, and a builder.

The invention also encompasses a method for cleaning a substrate selected from the group consisting of a hard surface and a fabric, comprising applying the composition of the present invention to the substrate.

EXPERIMENTS

Part ONE: Monomer Preparation

1. Synthesis of Monomer

The synthesis of the tri-substituted alkylphenol consisted of the controlled addition of two molar equivalents of styrene to an alkylphenol at elevated temperatures in the presence of a catalytic amount of acid to achieve the desired distyryl-substituted alkylphenol. The process typically generated distyryl alkylphenols at >90 mol % for the alkylphenols evaluated in the study. The distyryl alkylphenol generated in the first step was reacted with 25 molar equivalents of ethylene oxide (EO), using a catalyst, to give an ethoxylated distyryl alkylphenol. To achieve the conversion, a high reaction temperature and a reactor pressure were maintained throughout the EO feed. Once the EO charge was complete, the reaction mass was maintained, followed by cooling. The reaction mass was stripped of residual EO under reduced pressure and neutralized. The ethoxylated distyryl alkylphenol was then reacted with a molar excess of methacrylic anhydride in the presence of MEHQ and an air/NOx sparge to prevent undesirable polymerization. Methacrylic acid and water are added at the end of the reaction and the reaction mass is bottled as-is. In order to confirm the conversion of reagents into the desired products at the various steps, quantitative carbon NMR, acid value titration and Karl Fisher water analysis were utilized.

2. Characterization of Monomer 2.1: Quantitative 13C-NMR Analysis

Quantitative 13C-NMR is a convenient method of analysis used to confirm composition and structure. For the analysis of the Step 1 product, the distyryl alkylphenol is first dissolved in deuterated solvent, typically deuterated methanol, and analyzed using quantitative NMR techniques, such as appropriate number of scans, suitable relaxation times, and other parameters commonly known to NMR analysts. The resulting spectrum has peaks plotted as ppm of the total magnetic field, which correspond to the various carbons in the product composition based on their respective electronic environment. For example, in the analysis of distyryl nonylphenol (DSNP) via quantitative 13C-NMR, several carbon peaks in the NMR spectrum are useful for confirming the conversion of the nonylphenol to DSNP.

Spectrum 1: 13C-NMR Peak Identification for DSNP

For DSNP, the hydroxyl carbon has a peak at ~149 ppm with the substituted para-carbon at ~140 ppm. When the meta position is substituted, there is a peak at ~134 ppm with a second styryl ring carbon peak at 147 ppm. To confirm conversion of nonylphenol to DSNP (DiStyrylNonylPhenol), the hydroxyl carbon at ~150 ppm is set to 1.00 and the meta carbon (~134 ppm) and styryl ring carbon (~147 ppm) are compared. An integral of ~2 suggests complete conversion of nonylphenol to DSNP. The other carbons are less useful in quantifying the compositional components.

For the alkoxylation step of the process, quantitative carbon NMR is again very useful in determining the number of equivalents of ethylene oxide added to the disryryl alkylphenol, as well as quantifying the amount, if any, of undesirable polyethylene glycol (PEG) present in the alkoxylated product. The carbons of the EO backbone can be found at ~71 ppm, with the terminal hydroxyl carbon at ~61 ppm. For the analysis, the phenol carbon is set to 1.00 and the other carbons referenced to this. If the desirable equivalents of ethylene oxide were achieved, the total integral for the EO carbons (two carbons/EO) will be ~50 (50/2=25EO) and the terminal hydroxyl carbon will be ~1. A value of >1 for the hydroxyl carbon suggests the presence of PEG. For example, in the ethoxylation of DSNP with a target of 25 equivalents of EO, quantitative 13C-NMR showed ~26 equivalents EO (52.39/2) and 13 mol % (100%[1.27–1]/2).

Spectrum 2: 13C-NMR Peak Identification for Ethoxylated DSNP

For the final step of the process, quantitative carbon is useful for confirming the conversion of the alkoxylated intermediate into a methacrylate ester. In the conversion, the hydroxyl carbon at ~61 ppm shifts downfield to ~64 ppm and an ester carbonyl carbon peak will appear at ~168 ppm alongside the methacrylic acid carbonyl carbon peak at ~170 ppm. A peak at 61 ppm suggests incomplete conversion. Spectrum 3 shows a spectrum for DSNP-25EO Methacrylate Ester.

Spectrum 3: 13C-NMR Peak Identification for DSNP-25EO Methacrylate. For this example, complete conversion of the DSNP-25EO intermediate is confirmed by the lack of any peak at ~61 ppm and a peak having an integral of 1.08 at ~64 ppm. There is also further confirmation by the ester carbonyl peak (0.97) at ~168 ppm. Several other carbons have been labeled that help to confirm the overall structure of the molecule synthesized. Methacrylic acid, both inherent in the process and post-added to specification, can be quantified by the acid carbonyl carbon (5.68) at ~170 ppm.

2.2 Karl Fisher (% Water).

A Mettler-Toledo Karl Fisher automatic titrator was used to quantify the amount of water present in the final samples generated. A target of 20% water was established to match the commercially-available Sipomer SEM-25.

2.3 Acid Titration (% Methacrylic Acid)

Residual methacrylic acid, recorded as % methacrylic acid, was determined using an acid/base titration to a phenolphthalein endpoint. A target of 20% methacrylic acid was established to match the commercially-available Sipomer SEM-25.

2.4 Final % Actives (Calculation) & Specifications

Final % Actives:

1) Residual methacrylic acid, recorded as % methacrylic acid;
2) The moisture level (% water) is determined using Karl-Fisher titration;
3) The methacrylate ester, reported as % actives, is calculated by the following equation: % Methacrylate Ester=100%−% methacrylic acid−% water.

Monomer Properties:

The monomers of the study were synthesized using the process and conditions described previously. The distyryl nonylphenol was synthesized in duplicate to confirm reproducibility. Table 1 provides a summary of the final properties of the monomers synthesized.

TABLE 1

Monomer Properties

| Monomer Notebook # | Alkyl Group | Wt % H2O | Wt % Methacrylic Acid | Wt % Actives | Mol % Tri-substituted (NMR) | Mol % Di-substituted (NMR) | Equiv. EO (NMR) | Ethoxylated Intermediate NB# |
|---|---|---|---|---|---|---|---|---|
| R-1081-149 | Nonyl | 19.73 | 17.95 | 62.32 | >99 | <1 | 23.9 | R-1146-007 |
| R-1081-171 | Nonyl | 18.67 | 18.71 | 62.62 | >99 | <1 | 23.9 | R-1146-007 |
| R-1081-167 | t-Butyl | 17.80 | 17.36 | 64.84 | 97.4 | 2.6 | 24.6 | R-1146-025 |
| R-1081-185 | Methyl | 17.89 | 17.79 | 64.34 | 97.6 | 2.4 | 25.3 | R-1146-030 |
| R-1081-205 | Dodecyl | 18.93 | 18.31 | 62.76 | 93.7 | 6.3 | 25.2 | R-1146-048 |

From Table 1 it can be seen that the % Actives for the monomers synthesized in this study were slightly above the target 60% actives listed in the previous section. This was mainly due to the fact that the analyses of the monomers occurred off-line after the monomers had been bottled. In a plant setting, the analyses would be completed prior to drumming and adjustments made at that time. For this study, the latex recipes allowed for adjustment of the monomer charges to account for variations in the % actives.

Part TWO: HASE Preparation 2.1: Experimental Approach

HASE thickeners possess hydrophobic groups that interact with coating components to increase viscosity and modify rheology. In addition, their moderately high molecular weight polymer backbone also contributes to the thickening effect. Formulators modify the rheology by adding these thickening agents to water-based coatings to ensure appropriate appearance, storage and application properties. Since one of the mechanisms of thickening with the HASE-type rheological modifiers is based on interactions of the hydrophobe with components in the coating, the coating rheology is sensitive to changes in the hydrophobe. Therefore, to study the effect of changes in the hydrophobe on monomer performance, the various monomers were formulated into a HASE thickener and evaluated for their thickening efficiency. The thickening efficiency was then compared to the commercially-available Sipomer SEM-25. Emulsion polymerization of the HASE thickeners was performed via generally known procedures. Other reagents, such as protective colloids, buffers, chain transfer agents, etc. may be optionally added to positively affect the polymerization process and/or the final attributes of the latex generated.

Part THREE: HASE Thickening Efficiency 3.1: Following the synthesis of the HASE latex samples using the various novel and benchmark monomers, the samples were evaluated for thickening efficiency in an all-acrylic (Rhoplex SG-30) binder test formulation.

HASE thickeners under this experiment were based on a polyelectrolyte backbone, usually methacrylic acid and ethyl acrylate copolymer, with pendant hydrophobes (i.e., hydrophobes that are attached to the backbone with polyethylene oxide chains). It is, however, understood that with HASE thickeners the properties of the paint may change quite dramatically. A characteristic property of HASE thickeners is their sensitivity to variations in coating composition. Changes in type of binder, surfactant, and colorants can have a pronounced effect on paint viscosity. Therefore determination of KU thickening efficiency in a binder formulation is intended as a practical guide to test HASE thickeners.

3.2: Thickening Efficiency: For the analysis, the test HASE thickener, deionized water, Rhoplex SG-30, and 20% NH4OH were obtained. To a 250 ml jar was charged 108.0 g SG-30 and 61.0 g DI water. The pH was adjusted to 9.0-9.3. The jar was shaken gently and placed on a roller for ~1 hour. After one hour, a known amount of HASE thickener was charged to the jar with the goal of achieving a final KU of 95+2. After the HASE thickener addition, the jar was placed on a roller for 2-3 hours to ensure complete incorporation. The jar was removed from the roller and the final pH adjusted to 9.0-9.3. The KU and ICI viscosities are then evaluated and recorded. The results of the study are summarized in Table 2.

TABLE 2

Thickening Efficiency Results

| Hydrophobe Description | | Thickening Efficiency | | | |
|---|---|---|---|---|---|
| Sample Number | Sample Variation | Grams for KU 95 +/− 2 | KU Viscosity | ICI Viscosity | pH |
| R-1081-143 | Sipomer SEM-25 | 2.88 | 96.5 | 0.65 | 9.05 |
| R-1081-177 | Distyryl NonylPhenol-25EO Methacrylate | 1.75 | 95.3 | 0.30 | 9.02 |

When comparing the KU viscosity results in the SG-30 binder system, the novel distyryl nonylphenol-based monomer was found to be about 40% more efficient than the Sipomer SEM-25 based monomer benchmark.

It should be apparent embodiments other than those expressly described above come within the spirit and scope of the present invention. Thus, the present invention is not defined by the above description but by the claims appended hereto.

What is claimed is:

1. An ethylenically unsaturated monomer according to structure (D.I):

$$R^{18}\text{-}R^{14}\text{-}R^{13}\text{-}R^{12}\text{-}R^{11} \quad \text{(D.I)}.$$

$R^{12}$ is absent or is a bivalent linking group,
$R^{13}$ is bivalent polyether group,
$R^{14}$ is absent or is a bivalent linking group;
$R^{18}$ is a moiety having a site of ethylenic unsaturation; and
$R^{11}$ is a tri-substituted aromatic group according to the structure D.XII

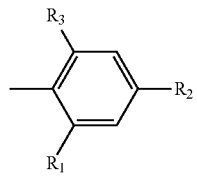

D.XII wherein $R_1$, $R_2$ and $R_3$ are independently selected from the following structures D.XIIIa, D.XIIIb, D.XIIIc, D.XIIId:

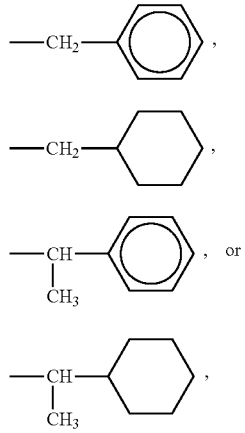

D.XIIIa

D.XIIIb

D.XIIIc

D.XIIId or a $C_9\text{-}C_{30}$ branched or linear alkyl group or alkenyl group;
wherein at least one of $R_1$, $R_2$ and $R_3$ is the $C_9\text{-}C_{30}$ branched or linear alkyl group or alkenyl group, and at least one of $R_1$, $R_2$ and $R_3$ is selected from structure D.XIIIa, D.XIIIb, D.XIIIc, or D.XIIId.

2. The ethylenically unsaturated monomer of claim 1 wherein $R_{13}$ is —[CH($R_{20}$)CH($R_{21}$)O]$_x$—, wherein x is an integer of from 0 to 100, and $R_{20}$ and $R_{21}$ are independently selected from any of the following:
H; —CH$_2$OH; phenyl; —CH$_2$Cl;
a $C_1\text{-}C_{30}$ straight or branched alkyl or alkenyl;
—CH$_2$OR$_{22}$ wherein $R_{22}$ is $C_1\text{-}C_{30}$ straight or branched alkyl or alkenyl, phenyl, or alkyl substituted phenyl; or R'COOCH$_2$— where R' is $C_1\text{-}C_{30}$ straight or branched alkyl or alkenyl.

3. The ethylenically unsaturated monomer of claim 1 wherein the monomer is according to structure D.XXX:

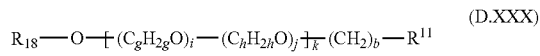

(D.XXX)

wherein:
g is an integer from 2 to 4;
h is an integer from 2 to 4;
b is an integer from 0 to 1;
k is an integer from 0 to 100;
i is an integer from 0 to 40;
j is an integer from 0 to 40;
$R^{18}$ is a moiety having a site of ethylenic unsaturation;
$R^{11}$ is according to structure D.XII

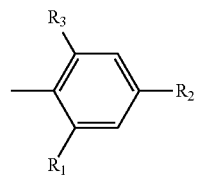

D.XII wherein $R_1$, $R_2$ and $R_3$ are independently selected from the following structures D.XIIIa, D.XIIIb, D.XIIIc, D.XIIId:

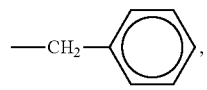

D.XIIIa

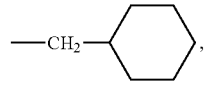

D.XIIIb

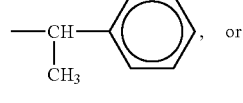

D.XIIIc

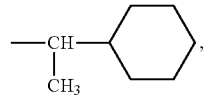

D.XIIId or a $C_9\text{-}C_{30}$ branched or linear alkyl group or alkenyl group;
wherein at least one of $R_1$, $R_2$ and $R_3$ is the $C_9\text{-}C_{30}$ branched or alkyl group or alkenyl group and at least one of $R_1$, $R_2$ and $R_3$ is selected from D.XIIIa, D.XIIIb, D.XIIIc, or D.XIIId.

4. The monomer of claim 3 wherein $R^{18}$ is according to structure (D.XV):

(D.XV)

wherein $R^{19}$ is H or $(C_1\text{-}C_4)$alkyl.

5. The monomer of claim 1 wherein the $C_9\text{-}C_{30}$ branched or linear alkyl group or alkenyl group is a $C_{10}\text{-}C_{30}$ branched or linear alkyl group.

6. The monomer of claim 1 wherein the $C_9$-$C_{30}$ branched or linear alkyl group or alkenyl group is a $C_{10}$-$C_{24}$ branched or linear alkenyl group.

7. The monomer of claim 1 wherein the $C_9$-$C_{30}$ branched or linear alkyl group or alkenyl group is a $C_9$-$C_{14}$ branched or linear alkenyl group.

8. The monomer of claim 1 wherein the $C_9$-$C_{30}$ branched or linear alkyl group or alkenyl group is a $C_{23}$-$C_{30}$ branched or linear alkenyl group.

9. The monomer of claim 1 wherein $R^{11}$ is a tri-substituted aromatic group according to the structure D.XII

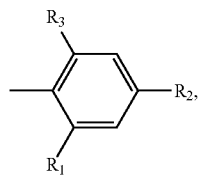

D.XII wherein $R_1$, $R_2$ and $R_3$ are independently selected from:
a styryl group, or
a $C_9$-$C_{30}$ branched or linear alkyl group or alkenyl group; wherein at least one of $R_1$, $R_2$ and $R_3$ is the $C_9$-$C_{30}$ branched or linear alkyl group or alkenyl group, and at least one of $R_1$, $R_2$ and $R_3$ is the styryl group.

10. The monomer of claim 1 wherein $R^{11}$ is a tri-substituted aromatic group according to the structure D.XII-1

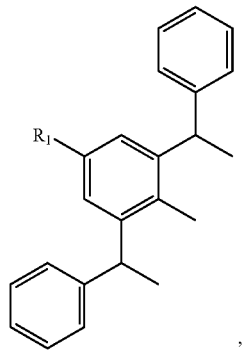

D.XII-1 wherein $R_1$, is the $C_9$-$C_{30}$ branched or linear alkyl group or alkenyl group.

11. The monomer of claim 10 wherein the $C_9$-$C_{30}$ branched or linear alkyl group or alkenyl group is a $C_9$-$C_{14}$ branched or linear alkyl group or alkenyl group.

12. A copolymer comprising at least one monomer according to structure D.XVI:

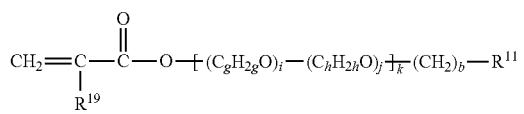

(D.XVI)

wherein:
g is an integer from 2 to 4;
h is an integer from 2 to 4;
b is an integer from 0 to 1;
k is an integer from 0 to 25;
i is an integer from 0 to 40;
j is an integer from 0 to 40;
$R^{19}$ is hydrogen; methyl or ethyl;
$R^{11}$ is according to structure D.XII

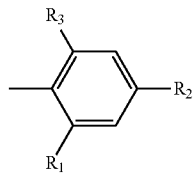

D.XII wherein $R_1$, $R_2$ and $R_3$ are independently selected from the following structures D.XIIIa, D.XIIIb, D.XIIIc, D.XIIId:

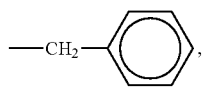

D.XIIIa

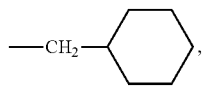

D.XIIIb

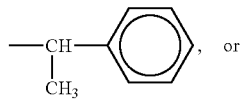

D.XIIIc

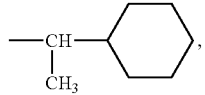

D.XIIId or a $C_9$-$C_{30}$ branched or linear alkyl group or alkenyl group; wherein at least one of $R_1$, $R_2$ and $R_3$ is the $C_9$-$C_{30}$ branched or linear alkyl group or alkenyl group and at least one of $R_1$, $R_2$ and $R_3$ is selected from structure D.XIIIa, D.XIIIb, D.XIIIc, D.XIIId.

13. A pH responsive copolymer of unsaturated copolymerizable monomers, said unsaturated copolymerizable monomers comprising, based on total weight of monomers:
A. about 0-60 weight percent of at least one $C_3$-$C_8$ alpha beta- ethylenically unsaturated acidic monomer, preferably a $C_3$-$C_8$ alpha beta-ethylenically unsaturated carboxylic acid monomer;
B. about 15-70 weight percent of at least one nonionic, copolymerizable $C_2$-$C_{12}$ alpha, beta-ethylenically unsaturated monomer; and
C. about 0.05 to 30 weight percent of at least one nonionic ethylenically unsaturated hydrophobic monomer according to claim 1.

14. The pH responsive copolymer of claim 13, comprising, based on total weight of monomers:
A. about 5 to 60 weight percent of the at least one $C_3$-$C_8$ alpha beta-ethylenically unsaturated acidic monomer, preferably a $C_3$-$C_8$ alpha beta-ethylenically unsaturated carboxylic acid monomer;
B. about 15-70 weight percent of the at least one nonionic, copolymerizable $C_2$-$C_{12}$ alpha, beta-ethylenically unsaturated monomer; and
C. about 0.05 to 30 weight percent of the at least one ethylenically unsaturated hydrophobic monomer according to structure D.XVI:

(D.XVI)

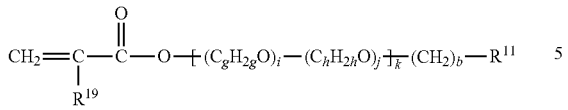

wherein:
g is an integer from 2 to 4;
h is an integer from 2 to 4;
b is an integer from 0 to 1;
k is an integer from 0 to 25;
i is an integer from 0 to 40;
j is an integer from 0 to 40;
$R^{19}$ is hydrogen; methyl or ethyl;
$R^{11}$ is a tri-substituted aromatic group according to the structure D.XII

D.XII

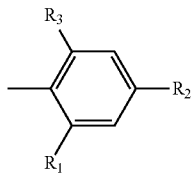

wherein $R_1$, $R_2$ and $R_3$ are independently selected from the following structures D.XIIIa, D.XIIIb, D.XIIIc, D.XIIId:

D.XIIIa

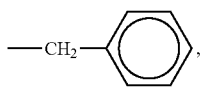

D.XIIIb

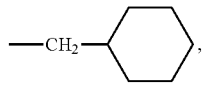

D.XIIIc

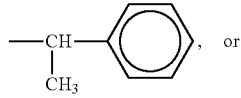, or

D.XIIId

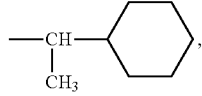, or a $C_2$-$C_{30}$ branched or linear alkyl group or alkenyl group; wherein at least one of $R_1$, $R_2$ and $R_3$ is the $C_2$-$C_{30}$ branched or linear alkyl group or alkenyl group and at least one of $R_1$, $R_2$ and $R_3$ is selected from structure D.XIIIa, D.XIIIb, D.XIIIc, D.XIIId.

15. The copolymer of claim 14, wherein the carboxylic acid monomer (A) is present from about 25 weight percent to about 60 weight percent based on total monomer weight.

16. The copolymer of claim 14, wherein the carboxylic acid monomer (A) is selected from a group consisting of methacrylic acid, acrylic acid and a combination thereof.

17. The copolymer of claim 14, wherein the nonionic monomer (B) is alkyl acrylate.

18. An aqueous composition, comprising water and the pH responsive copolymer of claim 14.

19. A method for thickening an aqueous emulsion, comprising: forming a blend by blending with the aqueous emulsion an amount of the pH-responsive composition of claim 17, effective to thicken the aqueous emulsion when pH of the blend is adjusted to a pH in the range of about 6.5 to about 11.

* * * * *